US010221190B2

(12) United States Patent
Kim et al.

(10) Patent No.: US 10,221,190 B2
(45) Date of Patent: Mar. 5, 2019

(54) BIGUANIDE COMPOUNDS AND USE THEREOF

(71) Applicant: IMMUNOMET THERAPEUTICS INC., Cambridge, MA (US)

(72) Inventors: Hong Woo Kim, Daejeon (KR); Ji Sun Lee, Daejeon (KR); Hye Jin Heo, Daejeon (KR); Hong Bum Lee, Daejeon (KR); Jae Kap Jeong, Daejeon (KR); Ji Hyun Park, Daejeon (KR); Seo-il Kim, Daejeon (KR); Young Woo Lee, Daejeon (KR)

(73) Assignee: ImmunoMet Therapeutics Inc., Houston, TX (US)

( * ) Notice: Subject to any disclaimer, the term of this patent is extended or adjusted under 35 U.S.C. 154(b) by 0 days.

(21) Appl. No.: 14/528,468

(22) Filed: Oct. 30, 2014

(65) Prior Publication Data
US 2015/0126518 A1    May 7, 2015

(30) Foreign Application Priority Data

Nov. 4, 2013   (KR) .................... 10-2013-0133156

(51) Int. Cl.
C07D 207/16    (2006.01)
C07D 211/60    (2006.01)
C07D 241/04    (2006.01)
C07D 401/12    (2006.01)
C07D 495/04    (2006.01)
C07D 405/12    (2006.01)

(52) U.S. Cl.
CPC ......... C07D 495/04 (2013.01); C07D 207/16 (2013.01); C07D 211/60 (2013.01); C07D 241/04 (2013.01); C07D 401/12 (2013.01); C07D 405/12 (2013.01)

(58) Field of Classification Search
None
See application file for complete search history.

(56) References Cited

U.S. PATENT DOCUMENTS

| 9,321,742 | B2 * | 4/2016 | Kim | ................. | C07D 333/20 |
| 9,540,325 | B2 * | 1/2017 | Kim | ................. | C07D 205/04 |
| 2014/0179660 | A1 * | 6/2014 | Kim | ................. | C07D 205/04 514/210.01 |
| 2014/0179661 | A1 * | 6/2014 | Kim | ................. | C07D 333/20 514/210.01 |

FOREIGN PATENT DOCUMENTS

| WO | WO 20/13/022278 | * | 2/2013 |
| WO | WO 2013/022279 | * | 2/2013 |

OTHER PUBLICATIONS

Williams et al. Foye's principles of medicinal chemistry, 5$^{th}$ edition, pp. 50 and 59-61, 2002.*
Tsubouchi et al. (Bioorganic & Medicinal Chemistry Letters, vol. 7, No. 13, pp. 1721-1724, 1997).*
Cairns et al., "Regulation of cancer cell metabolism"; Nature Reviews: Cancer, vol. 11, pp. 85-95, (2011).
Pollak, "Potential applications for biguanides in oncology", J Clin Invest., vol. 123, No. 9, pp. 3693-3700, (2013).

* cited by examiner

*Primary Examiner* — Anna Pagonakis
(74) *Attorney, Agent, or Firm* — Clark & Elbing LLP

(57) ABSTRACT

The present invention relates to biguanide compounds and use thereof, more particularly, to biguanide derivatives exhibiting excellent effects for inhibition of cancer cell proliferation and inhibition of cancer metastasis and recurrence, a method for preparing the same, a pharmaceutical composition containing the same as an active ingredient, and a method of prevention or treatment of cancer comprising the step of administering an effective amount of the composition to a subject in need thereof.

4 Claims, No Drawings

BIGUANIDE COMPOUNDS AND USE THEREOF

TECHNICAL FIELD

The present invention relates to biguanide compounds and use thereof, more particularly, to biguanide derivatives exhibiting excellent effects for inhibition of cancer cell proliferation and inhibition of cancer metastasis and recurrence, a method for preparing the same, and a pharmaceutical composition containing the same as an active ingredient. In addition, the present invention relates to a method of prevention and/or treatment of cancer comprising the step of administering an effective amount of the composition to a subject in need thereof.

RELATED ART

Normal cells produce ATP through oxidative phosphorylation and hardly produce lactic acid, while cancer cells produce ATP through glycolysis and lactic acid fermentation. Thus, cancer cells, unlike normal cells, require more glucose, and even under aerobic environment, are converted to pro-oncogenic metabolism wherein glucose prefers glycolysis (Warburg effect). Cancer cells use such a metabolic pathway for production of energy source as a main energy source, and thus, cancer cells make an environment where survival, proliferation, angiogenesis and metastasis can be actively progressed, and are progressed into malignant cancer. Therefore, if the energy metabolism of cancer cells is inhibited, it will be more likely to overcome narrow treatment area and tolerance problems of the existing target cancer agents, and recently, much concern has been focused on the development of cancer agents targeting metabolic characteristics of cancer cells (Nature Review cancer 2011; 11: 85-95).

Biguanide drugs such as phenformin and metformin are known as a mitochondria complex 1 inhibitor, and known to inhibit oxidative phosphorylation to increase energy stress of cancer cells, thereby inhibiting differentiation and survival of cancer cells. However, since the efficacies are insubstantial, there is a difficulty in development as anticancer agents. The use of phenformin has been thoroughly prohibited since the late 1970's due to the serious side effect of lactic acidosis. Thus, there is a demand for biguanide type material with improved chemicophysical properties, which exhibits more excellent pharmacological action than metformin and does not exhibit side effects like phenformin.

It has been reported that the oxidative phosphorylation capacity of metformin is insignificant, and thus, it is known that the anticancer effect is insignificant even if high dose is used (J. Clin. Invest. 2013; 123:3693-3700). Moreover, since it is absorbed through OCT1, the subject of cancer is limited to liver or pancreas (J Clin Invest. 2013; 123(9): 3693-3700). Meanwhile, it is reported that phenformin relatively effectively inhibits oxidative phosphorylation in cancer cells due to the property of the material, to decrease oxygen consumption rate (OCR), thus increasing extracellular acidification rate (ECAR) by the offset reaction. However, it is reported that in a patient group with problems of liver metabolism, lactic acidosis occurs, seriously causing death. As the result, the use as anti-diabetic has been prohibited in most countries including US. Accordingly, there is a demand for development of novel guanidine drugs that may overcome the disadvantages of the existing biguanide drugs, maintain the usefulness of the biguanide drugs and pharmacokinetically improve it, and induce combined effects with the existing drugs.

DISCLOSURE

Technical Problem

It is an object of the present invention to provide novel biguanide derivatives or pharmaceutically acceptable salts thereof that exhibit excellent effects for inhibiting cancer cell proliferation and effects for inhibiting cancer metastasis and recurrence even with a small amount, and a method for preparing the same.

It is another object of the present invention to provide an anticancer pharmaceutical composition comprising the compound or a pharmaceutically acceptable salt thereof as an active ingredient, wherein the cancer may be selected from the group consisting of uterine cancer, breast cancer, stomach cancer, brain cancer, rectal cancer, colorectal cancer, lung cancer, skin cancer, blood cancer and liver cancer.

It is another object of the present invention to provide a method of prevention and/or treatment of cancer that exhibits excellent inhibition effect of cancer cell proliferation and inhibition effect of cancer metastasis and recurrence even with a small amount compared to the existing drugs, comprising the step of administering the compound or a pharmaceutically acceptable salt thereof to a subject in need thereof.

Technical Solution

In order to achieve the objects, one embodiment of the invention provides novel biguanide derivatives or pharmaceutically acceptable salts thereof exhibiting excellent inhibition effect of cancer cell proliferation and inhibition effect of cancer metastasis and recurrence even with a small amount compared to the existing drugs, and a method for preparing the same, an anticancer pharmaceutical composition, a method of prevention and/or treatment of cancer. Specifically, the biguanide derivatives or pharmaceutically acceptable salts thereof are those selected from the group consisting of the compounds of the following Chemical Formula 1 to Chemical Formula 7.

As used herein, the term, 'a substituted group' refers to those where at least one hydrogen atom is replaced with at least one non-hydrogen atom group, provided that atomic valence requirement should be satisfied and a chemically stable compound should be generated from the substitution.

Unless explicitly described as 'unsubstituted' herein, it should be interpreted that all the substituents may be substituted or unsubstituted. $R_1$ to $R_3$ substituents in the biguanide derivative of the present invention may be independently substituted with at least one of the defined substituents.

A 'halogen' or 'halo' refers to fluoro, chloro, bromo and iodo. A 'hydroxy' group indicates —OH.

An 'alkyl' refers to a linear or branched saturated hydrocarbon having a specified number of carbon atoms (for example, 1 to 12 carbon atoms). Examples of the alkyl include, without limitation, methyl, ethyl, n-propyl, i-propyl, n-butyl, s-butyl, butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and n-octyl and the like. The alkyl may be attached to a parent group or a substrate at any ring atom, as long as it does not contravenes valence electron requirement. Similarly, the alkyl group may include at least one non-hydrogen substituent, as long as it does not contravene valence electron requirement. For example, a 'haloalkyl' is —CH₂(halo), —CH(halo)₂ or C(halo)₃, and it means a methyl group wherein at least one hydrogen of the methyl group is replaced with halogen. Examples of the 'haloalkyl' group include, without limitation, trifluoromethyl, trichloromethyl, tribromomethyl and triiodomethyl and the like.

The term 'alkoxy' refers to alkyl-O—, wherein the alkyl is as defined above. Examples of the alkoxy group include, without limitation, methoxy, ethoxy, n-propoxy, i-propoxy, n-butoxy, s-butoxy, t-butoxy, n-pentoxy, s-pentoxy and the like. The alkoxy may be attached to a parent group or a substrate at any ring atom, as long as it does not contravenes valence electron requirement. Similarly, the alkoxy group may include at least one non-hydrogen substituent, as long as it does not contravene valence electron requirement. For example, a 'haloalkoxy' is —O—CH₂(halo), —O—CH(halo)₂ or —OC(halo)₃, and it means a methyl group wherein at least one hydrogen of the methyl group is replaced with halogen. Examples of the 'haloalkoxy' group include, without limitation, trifluoromethoxy, trichloromethoxy, tribromomethoxy, and triiodomethoxy and the like.

A 'cycloalkyl' refers to saturated monocyclic and bicyclic hydrocarbon rings having a specified number of carbon atoms (namely, $C_{3-8}$ cycloalkyl refers to a cycloalkyl group having 3, 4, 5, 6, 7 or 8 carbon atoms as a ring member). The cycloalkyl may be attached to a parent group or a substrate at any ring atom, as long as it does not contravene valence electron requirement. Similarly, the cycloalkyl group may include at least one non-hydrogen substituent, as long as it does not contravene valence electron requirement.

A 'heterocycloalkyl' refers to 3 to 12-membered monocyclic and bicyclic hydrocarbon rings containing 1 to 3 heteroatoms selected from the group consisting of nitrogen, oxygen and sulfur. The heterocycloalkyl may be attached to a parent group or a substrate at any ring atom, as long as it does not contravene valence electron requirement. Similarly, the heterocycloalkyl group may include at least one non-hydrogen substituent, as long as it does not contravene valence electron requirement. Examples of the heterocycloalkyl include, without limitation, aziridine, azetidine, imidazolyl, pyrrolyl, pyrrolidinyl, piperidyl, morpholinyl, piperazinyl, azepanyl, indolyl, indolinyl and the like.

The term, 'aryl' refers to monovalent and divalent aromatic groups independently containing aromatic groups of a 5-membered and 6-membered monocycles, and the term, 'heteroaryl' refers to monovalent and divalent aromatic groups independently containing aromatic groups of 5-membered and 6-membered monocycles containing 1 to 4 heteroatoms independently selected from nitrogen, oxygen and sulfur. Examples of the 'heteroaryl' group include furanyl, pyrrolyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl, isoquinolinyl, carbazolyl, benzoxazolyl, benzodioxazolyl, benzothiazolyl, benzoimidazolyl, benzothiophenyl, triazinyl, phthalazinyl, quinolinyl, indolyl, benzofuranyl, purinyl and indolizinyl.

The present invention provides a biguanide derivative compound of the following Chemical Formula 1 or a pharmaceutically acceptable salt thereof:

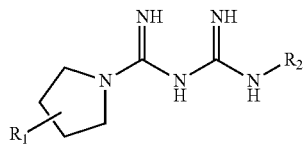

[Chemical Formula 1]

Wherein, $R_1$ is hydrogen, a hydroxy, or a linear or branched $C_{1-6}$ alkyl, and the $C_{1-6}$ alkyl is substituted by hydrogen or a hydroxy group, $R_2$ has the following Chemical Formula 11 or Chemical Formula 12, or is phenoxyphenyl, biphenyl, benzodioxol, or tetrahydronaphthalene,

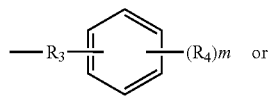

[Chemical Formula 11]

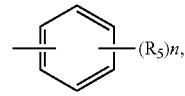

[Chemical Formula 12]

In the Chemical Formula 11, $R_3$ is a linear or branched $C_1$-$C_6$ alkyl, $R_4$ and $R_5$ of the Chemical Formula 11 and Chemical Formula 12, phenoxyphenyl, biphenyl, benzodioxol and naphthalene may be substituted by at least one substituent selected from the group consisting of hydrogen, halogen, $C_1$-$C_6$ alkyl unsubstituted or substituted by halogen, $C_1$-$C_6$ alkoxy unsubstituted or substituted by halogen, amine, $C_1$-$C_6$ alkylamine and amide, and m and n are independently an integer of 1 to 3.

Specific examples of the biguanide derivatives of the Chemical Formula according to the present invention are as follows:

N1-pyrrolidine-N5-(benzo[1,3]dioxol-5-ylmethyl) biguanide,
N1-pyrrolidine-N5-(4-methoxy)phenyl biguanide,
N1-pyrrolidine-N5-(3-chloro-4-methoxy)phenyl biguanide,
N1-pyrrolidine-N5-(2,6-difluoro-N5-methyl)phenyl biguanide,
N1-pyrrolidine-N5-(4-dimethylamino)phenyl biguanide,
N1-pyrrolidine-N5-(4-isopropyl)phenyl biguanide,
N1-pyrrolidine-N5-(3-phenoxy)phenyl biguanide,
N1-pyrrolidine-N5-(N-biphenyl-3-yl) biguanide,
N1-pyrrolidine-N5-(N-biphenyl-4-yl) biguanide,
N1-pyrrolidine-N5-(4'-fluorobiphenyl-3-yl) biguanide,
N1-pyrrolidine-N5-(3'-fluorobiphenyl-4-yl) biguanide,
N1-pyrrolidine-N5-(4-fluoro)phenethyl biguanide,
N1-pyrrolidine-N5-(2-phenylpropan-2-yl) biguanide,
N1-pyrrolidine-N5-(5,6,7,8-tetrahydronaphthalen-2-yl) biguanide,
N1-pyrrolidine-N5-(1,2,3,4-tetrahydronaphthalen-1-yl) biguanide,
N1-(S)-2-methyl pyrrolidine-N5-(4-(trifluoromethoxy)phenyl biguanide,
N1-(S)-3-hydroxy pyrrolidine-N5-(4-trifluoromethoxy)phenyl biguanide,
N1-(R)-3-hydroxy pyrrolidine-N5-(4-trifluoromethoxy) phenyl biguanide, N1-3-hydroxy methyl pyrrolidine-N5-(4-trifluoromethoxy) phenyl biguanide,
N1-pyrrolidine-N5-4-benzamide biguanide,
N-ethyl-4-((3-(imino(pyrrolidin-1-yl)methyl)guanidino) methyl)benzamide,
N-ethyl-3-((3-(imino(pyrrolidin-1-yl)methyl)guanidino) methyl)benzamide,
N1-pyrrolidine-N5-(4-(2-aminoethyl)phenyl biguanide,
N—(N-(4-(2-oxo-2-(piperidin-1-yl)ethylthio)phenyl)carbamimidoyl)pyrrolidine-1-carboximidamide, or
(S)-3-hydroxy-N—(N-(4-(2-oxo-2-(piperidin-1-yl)ethylthio)phenyl)carbamimidoyl)pyrrolidine-1-carboximidamide.

The compound of the Chemical Formula 1 according to the present invention may be prepared by the following illustrative method, and one specific example is as shown in the following Reaction Scheme 1.

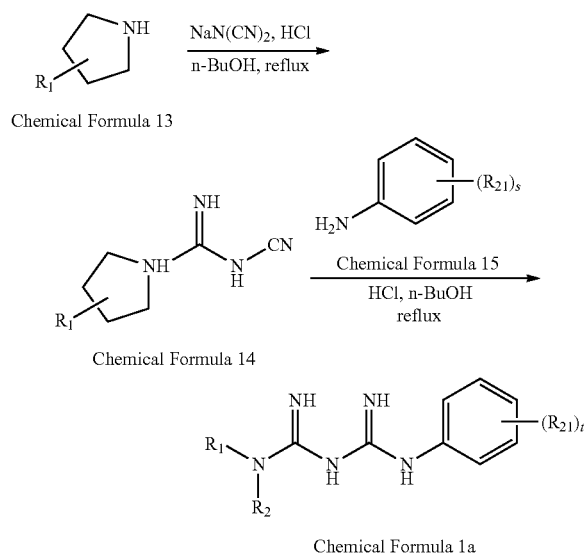

Reaction Scheme 1

Chemical Formula 13

Chemical Formula 14

Chemical Formula 1a

In the Reaction Scheme 1, $R_{21}$ is phenoxyphenyl, biphenyl, benzodioxol or naphthalene, which may be substituted by at least one selected from the group consisting of hydrogen, halogen, $C_1$-$C_6$ alkyl unsubstituted or substituted by halogen, $C_1$-$C_6$ alkoxy unsubstituted or substituted by halogen, amine, $C_1$-$C_6$ alkylamine and amide, and t is an integer of 1 to 3.

According to one example of the preparation method of the Chemical Formula 1, a cyanoguanidine compound of the Chemical Formula 14, which is used as an intermediate, may be obtained by reacting cyclic amine of the Chemical Formula 13 with dicyanamide such as sodium or potassium cyanamide in an organic solvent in the presence of acid. Subsequently, the cyanoguanidine compound of the Chemical Formula 14 is reacted under reflux with the Chemical Formula 15 in water, an organic solvent or a mixture thereof, to obtain a compound of the Chemical Formula 1a.

When preparing the cyanoguanidine compound of the Chemical Formula 14, the amount of dicyanoamide used is about 1 to 3 mole equivalents of the Chemical Formula 13, the amount of acid (for example, hydrochloric acid, sulfuric acid, nitric acid, bromic acid, 4-toluenesulfonic acid and the like) is about 1 to 2 mole equivalents of the Chemical Formula 13, and as the organic solvent, methanol, ethanol, propanol, butanol, pentanol, acetonitrile, benzene, toluene, 1,4-dioxane, N,N-dimethylamide and the like may be used. The reaction temperature may be 60 to 140° C., and the reaction time may be 3 to 24 hours.

The above obtained cyanoguanidine compound of the Chemical Formula 14 is dissolved in water, an organic solvent (for example, methanol, ethanol, propanol, butanol, pentanol, acetonitrile, benzene, toluene, 1,4-dioxane, N,N-dimethylamide and the like), or a mixture thereof, and then, the compound of the Chemical Formula 15 and acid (for example, hydrochloric acid, sulfuric acid, nitric acid, bromic acid, 4-toluenesulfonic acid and the like) are added, and the reaction mixture is stirred under reflux. Wherein, the amount of the compound of the Chemical Formula 15 is about 1 to 2 mole equivalents of the Compound 14, and the amount of acid is about 1 to 2 mole equivalents of the Compound 14. The reaction temperature is up to the reflux temperature of the solvent used (for example, in the case of butanol, 120 to 140° C.), and the reaction time is 6 to 24 hours. When the reaction is completed, the reaction solution is filtered, and then, the pH of the reaction solution is controlled to preferably about 4 to 5, for example, using acid such as hydrochloric acid, to concentrate and purify the produced solution, thereby obtaining the compound of the Chemical Formula 1 or a pharmaceutically acceptable salt thereof of the present invention.

The present invention also provides a biguanide derivative compound of the following Chemical Formula 2 or a pharmaceutically acceptable salt thereof:

[Chemical Formula 2]

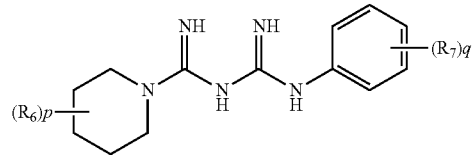

In the Chemical Formula 2,
$R_6$ is hydrogen, hydroxyl, or a linear or branched $C_1$-$C_6$ alkyl,
$R_7$ is independently hydrogen, halogen, $C_1$-$C_6$ alkyl unsubstituted or substituted by halogen, $C_1$-$C_6$ alkoxy unsubstituted or substituted by halogen, $C_1$-$C_6$ aminoalkyl, or phenoxy unsubstituted or substituted by halogen, and
p and q are independently an integer of 1 or 2.

Specific examples of the biguanide derivatives of the Chemical Formula 2 according to the present invention are as follows:
N1-4-hydroxy piperidine-N5-(4-trifluoromethoxy)phenyl biguanide,
N1-4-hydroxy piperidine-N5-(4-phenoxy)phenyl biguanide,
N1-4-hydroxy piperidine-N5-(3-phenoxy)phenyl biguanide,
N1-(2R,6S)-2,6-dimethylpiperidin-2-ylmethyl-N5-(4-(2-aminoethyl)phenyl biguanide,
N1-2-methyl piperidine-N5-(4-(2-aminoethyl)phenyl biguanide,
N1-3,5-dimethyl piperidine-N5-(4-(2-aminoethyl)phenyl biguanide, or
N1-3-methyl piperidine-N5-(4-(2-aminoethyl)phenyl biguanide.

The compound of the Chemical Formula 2 according to the present invention may be prepared by the following illustrative method, and one specific example is as shown in the following Reaction Scheme 2.

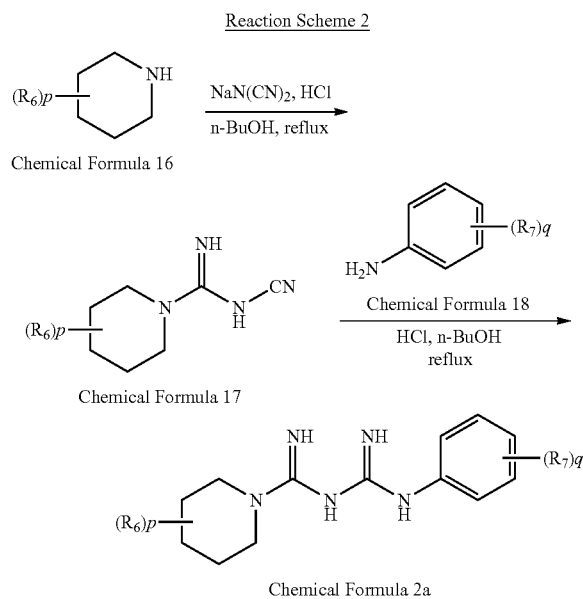

Reaction Scheme 2

Chemical Formula 16

Chemical Formula 17

Chemical Formula 18

Chemical Formula 2a

In the Reaction Scheme 2, $R_6$ is hydrogen, hydroxyl, or a linear or branched $C_1$-$C_6$ alkyl; $R_7$ is independently hydrogen, halogen, $C_1$-$C_6$ alkyl unsubstituted or substituted by halogen, $C_1$-$C_6$ alkoxy unsubstituted or substituted by halogen, $C_1$-$C_6$ aminoalkyl, or phenoxy unsubstituted or substituted by halogen; and p and q are independently an integer of 1 or 2.

According to the one example of the preparation method of the Chemical Formula 2a, the cyanoguanidine compound of the Chemical Formula 17, which is used as an intermediate, may be obtained by reacting the compound of the Chemical Formula 16 with dicyandiamide such as sodium or potassium cyanamide in an organic solvent in the presence of acid. Subsequently, the obtained cyanoguanidine compound of the Chemical Formula 17 is reacted under reflux with the Chemical Formula 18 in water, an organic solvent or a mixture thereof, to obtain the compound of the Chemical Formula 2a.

When preparing the cyanoguanidine compound of the Chemical Formula 17, the amount of dicyanoamide used is about 1 to 3 mole equivalents of the Chemical Formula 16, the amount of acid (for example, hydrochloric acid, sulfuric acid, nitric acid, bromic acid, 4-toluenesulfonic acid and the like) is about 1 to 2 mole equivalents of the Chemical Formula 16, and as the organic solvent, methanol, ethanol, propanol, butanol, pentanol, acetonitrile, benzene, toluene, 1,4-dioxane, N,N-dimethylamide and the like may be used. The reaction temperature may be 60 to 140° C., and the reaction time may be 3 to 24 hours.

The above obtained cyanoguanidine compound of the Chemical Formula 17 is dissolved in water, an organic solvent (for example, methanol, ethanol, propanol, butanol, pentanol, acetonitrile, benzene, toluene, 1,4-dioxane, N,N-dimethylamide and the like), or a mixture thereof, and then, the compound of the Chemical Formula 18 and acid (for example, hydrochloric acid, sulfuric acid, nitric acid, bromic acid, 4-toluenesulfonic acid and the like) are added, and the reaction mixture is stirred under reflux. Wherein, the amount of the compound of the Chemical Formula 18 is about 1 to 2 mole equivalents of the Compound 17, and the amount of acid is about 1 to 2 mole equivalents of the Compound 17. The reaction temperature is up to the reflux temperature of the solvent used (for example, in the case of butanol, 120 to 140° C.), and the reaction time is 6 to 24 hours. When the reaction is completed, the reaction solution is filtered, and then, the pH of the reaction solution is controlled to preferably about 4 to 5, for example, using acid such as hydrochloric acid, to concentrate and purify the produced solution, thereby obtaining the compound of the Chemical Formula 2a or a pharmaceutically acceptable salt thereof of the present invention.

The present invention provides a biguanide derivative compound of the following Chemical Formula 3 or a pharmaceutically acceptable salt thereof:

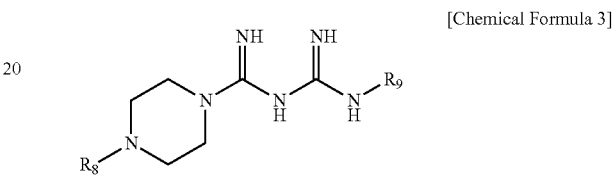

[Chemical Formula 3]

$R_8$ is hydrogen, or $C_1$-$C_6$ alkyl, $R_9$ is phenyl or benzyl, which is independently substituted by at least one selected from the group consisting of hydrogen, halogen, $C_1$-$C_6$ alkyl unsubstituted or substituted by halogen, $C_1$-$C_6$ alkoxy unsubstituted or substituted by halogen, and $C_1$-$C_6$ aminoalkyl.

Specific examples of the biguanide derivative of the Chemical Formula 3 according to the present invention are as follows:

N1-4-methyl piperazine-N5-(4-bromo)phenyl biguanide,
N1-4-methyl piperazine-N5-(3-bromo)phenyl biguanide,
N1-4-methyl piperazine-N5-(2-bromo)phenyl biguanide,
N1-4-methyl piperazine-N5-(3-bromo)benzyl biguanide,
N1-4-methyl piperazine-N5-(4-fluoro-3-trifluoromethyl) phenyl biguanide,
N1-4-methyl piperazine-N5-(3-chloro-4-trifluoromethoxy) phenyl biguanide,
N1-4-methyl piperazine-N5-(3-fluoro-4-trifluoromethoxy) phenyl biguanide,
N1-4-methyl piperazine-N5-(4-chloro-3-trifluoromethyl) phenyl biguanide,
N1-4-methyl piperazine-N5-(4-chloro-3-trifluoromethoxy) phenyl biguanide,
N1-4-methyl piperazine-N5-(4-fluoro-3-trifluoromethoxy) phenyl biguanide,
N1-4-methyl piperazine-N5-(4-fluoro-3-trifluoromethoxy) benzyl biguanide,
N1-4-methyl piperazine-N5-(3-fluoro-4-trifluoromethyl) benzyl biguanide,
N1-4-methyl piperazine-N5-(3-fluoro-4-trifluoromethoxy) benzyl biguanide,
N1-4-methyl piperazine-N5-(3-fluoro-4-trifluoromethyl) phenyl biguanide, or
N1-4-ethyl piperazine-N5-(4-trifluoromethoxy)phenyl biguanide.

The compound of the Chemical Formula 3 according to the present invention may be prepared by the following illustrative method, and one specific example is as shown in the following Reaction Scheme 3.

Reaction Scheme 3

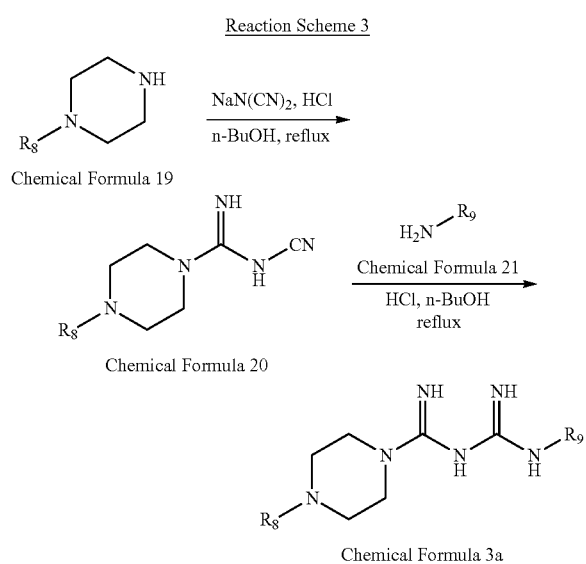

Chemical Formula 19

Chemical Formula 20

Chemical Formula 3a

In the Reaction Scheme 3, $R_8$ is hydrogen, or $C_1$-$C_6$ alkyl, $R_9$ is phenyl or benzyl, which is independently substituted by at least one selected from the group consisting of hydrogen, halogen, $C_1$-$C_6$ alkyl unsubstituted or substituted by halogen, $C_1$-$C_6$ alkoxy unsubstituted or substituted by halogen, and $C_1$-$C_6$ aminoalkyl.

According to one example of the preparation method of the Chemical Formula 3a, a cyanoguanidine compound of the Chemical Formula 20, which is used as an intermediate, may be obtained by reacting the compound of the Chemical Formula 19 with dicyanamide such as sodium or potassium cyanamide in an organic solvent in the presence of acid. Subsequently, the cyanoguanidine compound of the Chemical Formula 20 is reacted under reflux with the Chemical Formula 21 in water, an organic solvent or a mixture thereof, to obtain a compound of the Chemical Formula 3a.

When preparing the cyanoguanidine compound of the Chemical Formula 20, the amount of dicyanoamide used is about 1 to 3 mole equivalents of the Chemical Formula 19, the amount of acid (for example, hydrochloric acid, sulfuric acid, nitric acid, bromic acid, 4-toluenesulfonic acid and the like) is about 1 to 2 mole equivalents of the Chemical Formula 19, and as the organic solvent, methanol, ethanol, propanol, butanol, pentanol, acetonitrile, benzene, toluene, 1,4-dioxane, N,N-dimethylamide and the like may be used. The reaction temperature may be 60 to 140° C., and the reaction time may be 3 to 24 hours.

The above obtained cyanoguanidine compound of the Chemical Formula 20 is dissolved in water, an organic solvent (for example, methanol, ethanol, propanol, butanol, pentanol, acetonitrile, benzene, toluene, 1,4-dioxane, N,N-dimethylamide and the like), or a mixture thereof, and then, the compound of the Chemical Formula 21 and acid (for example, hydrochloric acid, sulfuric acid, nitric acid, bromic acid, 4-toluenesulfonic acid and the like) are added, and the reaction mixture is stirred under reflux. Wherein, the amount of the compound of the Chemical Formula 21 used is about 1 to 2 mole equivalents of the Compound 20, and the amount of acid used is about 1 to 2 mole equivalents of the Compound 20. The reaction temperature is up to the reflux temperature of the solvent used (for example, in the case of butanol, 120 to 140° C.), and the reaction time is 6 to 24 hours. When the reaction is completed, the reaction solution is filtered, and then, the pH of the reaction solution is controlled to preferably about 4 to 5, for example, using acid such as hydrochloric acid, to concentrate and purify the produced solution, thereby obtaining the compound of the Chemical Formula 3a or a pharmaceutically acceptable salt thereof of the present invention.

The present invention provides a biguanide derivative compound of the following Chemical Formula 4 or a pharmaceutically acceptable salt thereof:

[Chemical Formula 4]

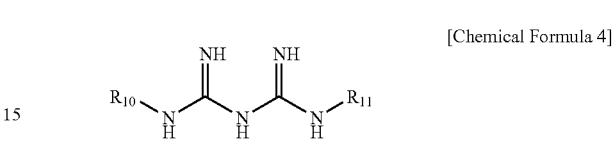

Wherein, $R_{10}$ is a substituent derived from phenyl, phenoxyphenyl, piperidine, pyridine, dihydropyridine, pyrazine, pyrrolidine, piperidine, cyclopentane, or furane, which may be substituted by at least one substituted selected from the group consisting of hydrogen, halogen, $C_1$-$C_6$ alkyl unsubstituted or substituted by halogen, $C_1$-$C_6$ alkoxy unsubstituted or substituted by halogen, and sulfonyl, $R_{11}$ is independently a phenyl, a biphenyl, or a benzyl group, which may be substituted by at least one substituent selected from the group consisting of hydrogen, halogen, $C_1$-$C_6$ alkyl unsubstituted or substituted by halogen, and $C_1$-$C_6$ alkoxy unsubstituted or substituted by halogen.

Specific examples of the biguanide derivative of the Chemical Formula 4 according to the present invention are as follows:

N1-3-pyridine-N5-(4-trifluoromethyl)phenyl biguanide,
N1-3-pyridine-N5-(4-trifluoromethoxy)phenyl biguanide,
N1-3-pyridine-N5-(4-trifluoromethyl)benzyl biguanide,
N1-3-pyridine-N5-(4-fluoro-3-trifluoromethyl)phenyl biguanide,
N1-2-pyrazine-N5-(4-trifluoromethoxy)phenyl biguanide
N1-2-pyrazine-N5-(4-trifluoromethyl)phenyl biguanide,
N1-cyclopentyl-N5-(4-trifluoromethoxy)phenyl biguanide,
N1-cyclopentyl-N5-(4-fluoro)phenyl biguanide,
N1-furan-2-ylmethyl-N5-(4-chloro)phenyl biguanide,
N1-furan-2-ylmethyl-N5-(4-trifluoromethoxy)phenyl biguanide,
N1-furan-2-ylmethyl-N5-(4-trifluoromethyl)phenyl biguanide,
N1-dihydropyridine-N5-(4-(2-aminoethyl)phenyl biguanide,
N1-phenyl-N5-(3-trifluoromethyl)benzyl biguanide,
N1-4-trifluoromethoxy phenyl-N5-(N-biphenyl-4-yl) biguanide,
N1-3,3-difluoro pyrrolidine-N5-(4-trifluoromethoxy)phenyl biguanide,
N1-4,4-difluoro piperidine-N5-(4-trifluoromethoxy)phenyl biguanide,
N1-4-(methylsulfonyl)piperidine-N5-(4-trifluoromethoxy)phenyl biguanide, or
N1-3-phenoxyphenyl-N5-(4-trifluoromethoxy)phenyl biguanide.

The compound of the Chemical Formula 4 according to the present invention may be prepared by the following illustrative method, and one specific example is as shown in the following Reaction Scheme 4.

Reaction Scheme 4

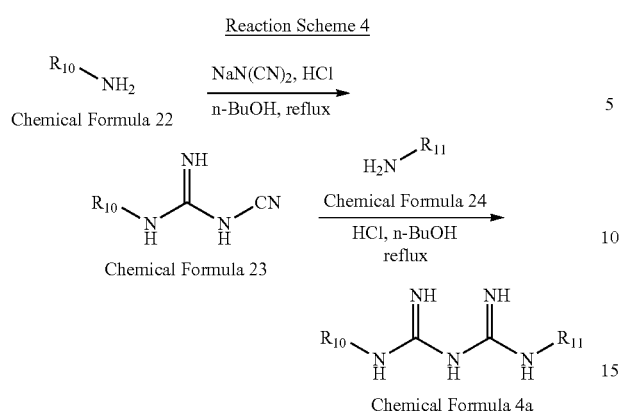

Chemical Formula 4a

In the Reaction Scheme 4, $R_{10}$ is a substituent derived from phenyl, phenoxyphenyl, piperidine, pyridine, dihydropyridine, pyrazine, pyrrolidine, piperidine, cyclopentane, or furane, which may be substituted by at least one substituent selected from the group consisting of hydrogen, halogen, $C_1$-$C_6$ alkyl unsubstituted or substituted by halogen, $C_1$-$C_6$ alkoxy unsubstituted or substituted by halogen, and sulfonyl, $R_{11}$ is independently a phenyl, a biphenyl, or a benzyl group, which may be substituted by at least one substituent selected from the group consisting of hydrogen, halogen, $C_1$-$C_6$ alkyl unsubstituted or substituted by halogen, and $C_1$-$C_6$ alkoxy unsubstituted or substituted by halogen.

According to one example of the preparation method of the Chemical Formula 4a, a cyanoguanidine compound of the Chemical Formula 23, which is used as an intermediate, may be obtained by reacting the compound of the Chemical Formula 22 with dicyanamide such as sodium or potassium cyanamide in an organic solvent in the presence of acid. Subsequently, the cyanoguanidine compound of the Chemical Formula 23 is reacted under reflux with the Chemical Formula 24 in water, an organic solvent or a mixture thereof, to obtain a compound of the Chemical Formula 4a.

When preparing the cyanoguanidine compound of the Chemical Formula 23, the amount of dicyanoamide used is about 1 to 3 mole equivalents of the Chemical Formula 22, the amount of acid (for example, hydrochloric acid, sulfuric acid, nitric acid, bromic acid, 4-toluenesulfonic acid and the like) is about 1 to 2 mole equivalents of the Chemical Formula 22, and as the organic solvent, methanol, ethanol, propanol, butanol, pentanol, acetonitrile, benzene, toluene, 1,4-dioxane, N,N-dimethylamide and the like may be used. The reaction temperature may be 60 to 140° C., and the reaction time may be 3 to 24 hours.

The above obtained cyanoguanidine compound of the Chemical Formula 23 is dissolved in water, an organic solvent (for example, methanol, ethanol, propanol, butanol, pentanol, acetonitrile, benzene, toluene, 1,4-dioxane, N,N-dimethylamide and the like), or a mixture thereof, and then, the compound of the Chemical Formula 24 and acid (for example, hydrochloric acid, sulfuric acid, nitric acid, bromic acid, 4-toluenesulfonic acid and the like) are added, and the reaction mixture is stirred under reflux. Wherein, the amount of the compound of the Chemical Formula 24 used is about 1 to 2 mole equivalents of the Compound 23, and the amount of acid used is about 1 to 2 mole equivalents of the Compound 23. The reaction temperature is up to the reflux temperature of the solvent used (for example, in the case of butanol, 120 to 140° C.), and the reaction time is 6 to 24 hours. When the reaction is completed, the reaction solution is filtered, and then, the pH of the reaction solution is controlled to preferably about 4 to 5, for example, using acid such as hydrochloric acid, to concentrate and purify the produced solution, thereby obtaining the compound of the Chemical Formula 4a or a pharmaceutically acceptable salt thereof of the present invention.

The present invention provides a biguanide derivative compound of the following Chemical Formula 5 or a pharmaceutically acceptable salt thereof:

[Chemical Formula 5]

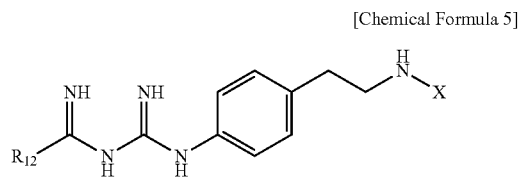

Wherein, X is a compound of the following Chemical Formula 15 or Chemical Formula 16:

[Chemical Formula 15]

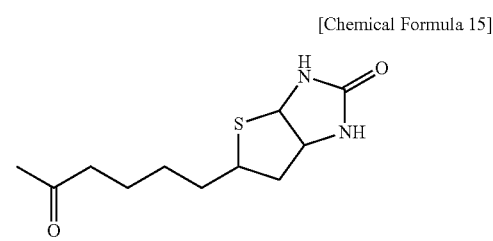

[Chemical Formula 16]

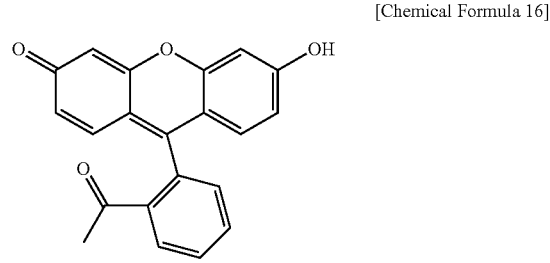

$R_{12}$ is pyrrolidine, piperidine, or dihydropyridine, which is independently substituted by at least one selected from the group consisting of hydrogen, halogen, $C_1$-$C_6$ alkyl unsubstituted or substituted by halogen, $C_1$-$C_6$ alkoxy unsubstituted or substituted by halogen, and $C_1$-$C_6$ aminoalkyl.

Specific examples of the biguanide derivative of the Chemical Formula 5 according to the present invention are as follows:

N-(4-(3-(imino(pyrrolidin-1-yl)methyl)guanidino)phenethyl)-5-(2-oxohexahydro-1H-thieno[2,3-d]imidazol-5-yl)pentanamide, N-(4-(3-(imino(2-methylpiperidin-1-yl)methyl)guanidino)phenethyl)-5-(2-oxohexahydro-1H-thieno[2,3-d]imidazol-5-yl)pentanamide, N-(4-(3-((3,5-dimethylpiperidin-1-yl)(imino)methyl)guanidino)phenethyl)-5-(2-oxohexahydro-1H-thieno[2,3-d]imidazol-5-yl)pentanamide, N-(4-(3-((5,6-dihydropyridin-1(2H)-yl)(imino)methyl)guanidino)phenethyl)-5-(2-oxohexahydro-1H-thieno[2,3-d]imidazol-5-yl)pentanamide, N-(4-(3-(((2R,6S)-2,6-dimethylpiperidin-1-yl)(imino)methyl)guanidino)phenethyl)-5-(2-oxohexahydro-1H-thieno[2,3-d]imidazol-5-yl)pentanamide, N-(4-(3-(imino(pyrrolidin-1-yl)methyl)guanidino)phenyl)-5-(2-oxohexahydro-1H-thieno[2,3-d]imidazol-5-yl)pentanamide, 2-(6-hydroxy-3-oxo-3H-xanthen-9-yl)-N-(4-(3-(imino(pyrrolidine-1-yl)methyl)guanidino)benzyl)benzamide, N-(4-(3-(((2R,6S)-2,6-dimethylpiperidin-1-yl)(imino)methyl)guanidino)benzyl)-2-(6-hydroxy-3-oxo-3H-xanthen-9-yl)benzamide, N-(4-(3-((3,5-dimethylpiperidin-1-yl)(imino)methyl)guanidino)benzyl)-2-(6-hydroxy-3-oxo-3H-xanthen-9-yl)benzamide, or 2-(6-hydroxy-3-oxo-3H-xanthen-9-yl)-N-(4-(3-(imino(3-methylpiperidin-1-yl)methyl)guanidino)benzyl)benzamide.

The compound of the Chemical Formula 5 according to the present invention may be prepared by the following illustrative method, and one specific example is as shown in the following Reaction Scheme 5.

Reaction Scheme 5

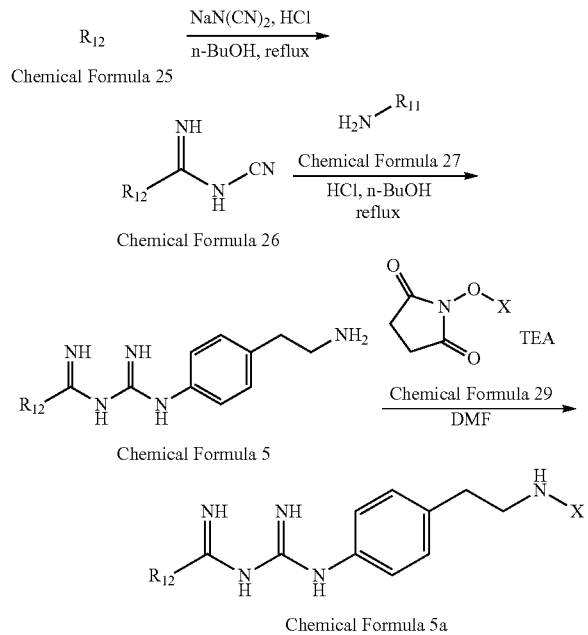

In the Reaction Scheme 5, $R_{12}$ is pyrrolidine, piperidine, or dihydropyridine, which is independently substituted by at least one selected from the group consisting of hydrogen, halogen, $C_1$-$C_6$ alkyl unsubstituted or substituted by halogen, $C_1$-$C_6$ alkoxy unsubstituted or substituted by halogen, and $C_1$-$C_6$ aminoalkyl; and X is a compound of the Chemical Formula 15 or Chemical Formula 16.

According to one example of the preparation method of the Chemical Formula 5a, a cyanoguanidine compound of the Chemical Formula 26, which is used as an intermediate, may be obtained by reacting the compound of the Chemical Formula 25 with dicyanamide such as sodium or potassium cyanamide in an organic solvent in the presence of acid. Subsequently, the cyanoguanidine compound of the Chemical Formula 26 is reacted under reflux with the Chemical Formula 27 in water, an organic solvent or a mixture thereof, to obtain a compound of the Chemical Formula 5. The compound of the Chemical Formula 5 and a compound of the Chemical Formula 29 are stirred in dimethylformamide at room temperature to obtain a compound of the Chemical Formula 5a or a pharmaceutically acceptable salt thereof.

When preparing the cyanoguanidine compound of the Chemical Formula 26, the amount of dicyanoamide used is about 1 to 3 mole equivalents of the Chemical Formula 25, the amount of acid (for example, hydrochloric acid, sulfuric acid, nitric acid, bromic acid, 4-toluenesulfonic acid and the like) is about 1 to 2 mole equivalents of the Chemical Formula 25, and as the organic solvent, methanol, ethanol, propanol, butanol, pentanol, acetonitrile, benzene, toluene, 1,4-dioxane, N,N-dimethylamide and the like may be used. The reaction temperature may be 60 to 140° C., and the reaction time may be 3 to 24 hours.

The above obtained cyanoguanidine compound of the Chemical Formula 26 is dissolved in water, an organic solvent (for example, methanol, ethanol, propanol, butanol, pentanol, acetonitrile, benzene, toluene, 1,4-dioxane, N,N-dimethylamide and the like), or a mixture thereof, and then, the compound of the Chemical Formula 27 and acid (for example, hydrochloric acid, sulfuric acid, nitric acid, bromic acid, 4-toluenesulfonic acid and the like) are added, and the reaction mixture is stirred under reflux. Wherein, the amount of the compound of the Chemical Formula 27 used is about 1 to 2 mole equivalents of the Compound 26, and the amount of acid used is about 1 to 2 mole equivalents of the Compound 26. The reaction temperature is up to the reflux temperature of the solvent used (for example, in the case of butanol, 120 to 140° C.), and the reaction time is 6 to 24 hours. When the reaction is completed, the reaction solution is filtered, and then, the pH of the reaction solution is controlled to preferably about 4 to 5, for example, using acid such as hydrochloric acid, to concentrate and purify the produced solution, thereby obtaining the compound of the Chemical Formula 5. The compound of the Chemical Formula 5 and a compound of the Chemical Formula 29 are dissolved in dimethylformamide, and then, trimethylamine is added. After stirring at room temperature for 24 hours, distillation under reduced pressure and chromatogram affords a compound of the Chemical Formula 5a or a pharmaceutically acceptable salt thereof according to the present invention The present invention provides a biguanide derivative compound of the following Chemical Formula 6 and a pharmaceutically acceptable salt thereof:

[Chemical Formula 6]

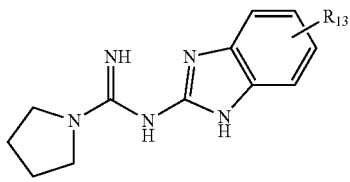

Wherein, $R_{13}$ is at least one selected from the group consisting of hydrogen, halogen, $C_1$-$C_6$ alkyl unsubstituted or substituted by halogen, $C_1$-$C_6$ alkoxy unsubstituted or substituted by halogen, and $C_1$-$C_6$ aminoalkyl.

Specific examples of the biguanide derivative of the Chemical Formula 6 according to the present invention are as follows:

N-(5-(trifluoromethoxy)-1H-benzo[d]imidazol-2-yl)pyrrolidine-carboximidamide,

N-(5-fluoro-1H-benzo[d]imidazol-2-yl)pyrrolidine-1-carboximidamide,

N-(5-methyl-1H-benzo[d]imidazol-2-yl)pyrrolidine-1-car-
  boximidamide,
N-(5-methoxy-1H-benzo[d]imidazol-2-yl)pyrrolidine-1-
  carboximidamide, or
N-(1H-benzo[d]imidazol-2-yl)pyrrolidine-1-carboximid-
  amide.

The compound of the Chemical Formula 6 according to the present invention may be prepared by the following illustrative method, and one specific example is as shown in the following Reaction Scheme 6.

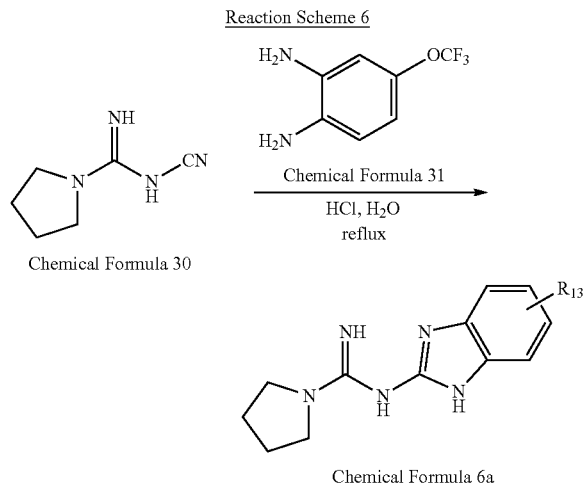

In the Reaction Scheme 6, $R_{13}$ is at least one selected from the group consisting of hydrogen, halogen, $C_1$-$C_6$ alkyl unsubstituted or substituted by halogen, $C_1$-$C_6$ alkoxy unsubstituted or substituted by halogen, and $C_1$-$C_6$ aminoalkyl.

According to one example of the preparation method of the Chemical Formula 6a, a cyanoguanidine compound of the Chemical Formula 30, which is used as an intermediate, may be obtained by the reaction as shown in the Reaction Scheme 1. Subsequently, the cyanoguanidine compound of the Chemical Formula 30 is reacted under reflux with the Chemical Formula 31 in water, an organic solvent or a mixture thereof, to obtain a compound of the Chemical Formula 6a.

After dissolving the cyanoguanidine compound of the Chemical Formula 30 in water, the compound of the Chemical Formula 31 and acid (for example, hydrochloric acid, sulfuric acid, nitric acid, bromic acid, 4-toluenesulfonic acid and the like) are added, and the reaction mixture is stirred under reflux. Wherein, the amount of the compound of the Chemical Formula 31 used is about 1 to 2 mole equivalents of the Compound 30, and the amount of acid used is about 1 to 2 mole equivalents of the Compound 30. The reaction temperature is up to the reflux temperature of the solvent used (for example, in the case of butanol, 120 to 140° C.), and the reaction time is 6 to 24 hours. When the reaction is completed, the reaction solution is filtered, and then, the pH of the reaction solution is controlled to preferably about 4 to 5, for example, using acid such as hydrochloric acid, to concentrate and purify the produced solution, thereby obtaining the compound of the Chemical Formula 6a or a pharmaceutically acceptable salt thereof.

The present invention provides a biguanide derivative compound of the following Chemical Formula 7 or a pharmaceutically acceptable salt thereof:

[Chemical Formula 7]

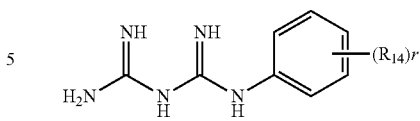

Wherein, $R_{14}$ is independently selected from hydrogen, halogen, $C_1$-$C_6$ alkyl unsubstituted or substituted by halogen, $C_1$-$C_6$ alkoxy unsubstituted or substituted by halogen, $C_1$-$C_6$ thioalkyl unsubstituted or substituted by halogen, and $C_1$-$C_6$ aminoalkyl, and r is an integer of 1 to 3.

Specific examples of the biguanide derivative of the Chemical Formula 7 according to the present invention are as follows:
N5-(2,4-dichloro)phenyl biguanide
N5-4-fluorophenyl biguanide
N5-(3,4-dichloro)phenyl biguanide
N5-(2-chloro-5-trifluoromethyl)phenyl biguanide
N5-(3-chloro-4-fluoro)phenyl biguanide
N5-(2,3-dichloro)phenyl biguanide
N5-(4-trifluoromethylthio)phenyl biguanide, or
N1,N1-dimethyl-N5-4-(2-oxo-2-(piperidin-1-yl)ethylthio)
  phenyl biguanide.

The compound of the Chemical Formula 7 according to the present invention may be prepared by the following illustrative method, and one specific example is as shown in the following Reaction Scheme 7.

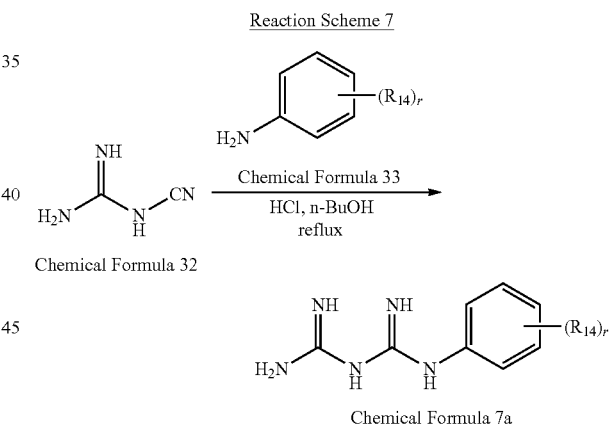

In the Reaction Scheme 7, $R_{14}$ is independently selected from the group consisting of hydrogen, halogen, $C_1$-$C_6$ alkyl unsubstituted or substituted by halogen, $C_1$-$C_6$ alkoxy unsubstituted or substituted by halogen, $C_1$-$C_6$ thioalkyl unsubstituted or substituted by halogen, and $C_1$-$C_6$ aminoalkyl.

According to one example of the preparation method of the Chemical Formula 7a, a cyanoguanidine compound of the Chemical Formula 32 is reacted under reflux with a compound of the Chemical Formula 33 in water, an organic solvent or a mixture thereof, to obtain a compound of the Chemical Formula 7a.

After dissolving the cyanoguanidine compound of the Chemical Formula 32 in water, an organic solvent (for example, methanol, ethanol, propanol, butanol, pentanol, acetonitrile, benzene, toluene, 1,4-dioxane, N,N-dimethylamide and the like), or a mixture thereof, the compound of the Chemical Formula 33 and acid (for example, hydrochloric acid, sulfuric acid, nitric acid, bromic acid, 4-toluenesulfonic acid and the like) are added, and the reaction mixture is stirred under reflux. Wherein, the amount of the compound of the Chemical Formula 33 used is about 1 to 2 mole equivalents of the Compound 32, and the amount of acid used is about 1 to 2 mole equivalents of the Compound 32. The reaction temperature is up to the reflux temperature of the used solvent (for example, in the case of butanol, 120 to 140° C.), and the reaction time is 6 to 24 hours. After the reaction is completed, the reaction solution is filtered, and then, the pH of the reaction solution is controlled to preferably about 4 to 5, for example, using acid such as hydrochloric acid and the like, to concentrate and purify the produced solution, thereby obtaining a compound of the Chemical Formula 7a or a pharmaceutically acceptable salt thereof according to the present invention.

Further specific examples of the biguanide compounds according to the present invention include the following compounds:

(E)-N—(N-(4-(3-oxo-3-(piperidin-1-yl)prop-1-enyl)phenyl)carbamimidoyl)pyrrolidine-1-carboximidamide, N—(N-(4-(piperidine-1-carbonyl)benzyl)carbamimidoyl) pyrrolidine-1-carboximidamide, N—(N-(4-(3-oxo-3-(piperidin-1-yl)propyl)phenyl)carbamimidoyl)pyrrolidine-1-carboximidamide N—(N-(4-(trifluoromethoxy)phenyl)carbamimidoyl)-3,4-dihydroisoquinolin-2(1H)-carboximidamide, N—(N-(4-(trifluoromethoxy)phenyl)carbamimidoyl)indoline-1-carboximidamide, N-(imino(pyrrolidin-1-yl)methyl)-3,4-dihydroisoquinolin-2 (1H)-carboximidamide, N—(N-(4-phenoxyphenyl)carbamimidoyl)indoline-1-carboximidamide, or N—(N-(3-phenoxyphenyl)carbamimidoyl)indoline-1-carboximidamide.

Meanwhile, the pharmaceutically acceptable salt of the compound according to the present invention may be an acid addition salt formed using organic acid or inorganic acid. The organic acid may include, for example, formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, dichloroacetic acid, aminooxy acetic acid, benzenesulfonic acid, 4-toluenesulfonic acid and methanesulfonic acid salts; inorganic acid may include, for example, hydrochloric acid, hydrobromic acid, sulfuric acid, phosphoric acid, nitric acid, carbonic acid, and boric acid salts. The acid addition salt may be prepared by a common preparation method of salts, such as a) directly mixing the compound of the Chemical Formula 1 and acid, b) dissolving the compound of the Chemical Formula 1 or acid in a solvent or a an aqueous solvent and mixing them, or c) mixing the compound of the Chemical Formula 1 and acid in a solvent or an aqueous solvent.

According to specific embodiment, the pharmaceutically acceptable salt of the compound of the Chemical Formula 1 may be a salt of acid selected from the group consisting of formic acid, acetic acid, propionic acid, lactic acid, butyric acid, isobutyric acid, triflouroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid and boric acid.

As described in the following Experimental Examples, cancer cell proliferation inhibition effect of the biguanide compounds according to the present invention was confirmed by measuring the concentration value at which growth of cell line is inhibited to 50% (cell growth inhibition concentration, $IC_{50}$) using human melanoma-derived cell line, pancreatic cancer-derived cell line, and human colorectal cancer-derived cell line.

Thus, another embodiment of the present invention provides a pharmaceutical composition comprising the biguanide compound or a pharmaceutical salt thereof as an active ingredient. The pharmaceutical composition according to the present invention has excellent cancer cell proliferation inhibition effect, and thus, it may be used as an anticancer agent for various cancers, and specific examples of the cancer include uterine cancer, breast cancer, stomach cancer, brain cancer, rectal cancer, colorectal cancer, lung cancer, skin cancer, blood cancer and liver cancer, but not limited thereto.

The present invention also relates to a method of prevention and/or treatment of cancer that exhibits excellent cancer cell proliferation inhibition effect and cancer metastasis and recurrence inhibition effect even with a small amount, comprising the step of administering the compound or a pharmaceutically acceptable salt thereof to a subject in need thereof. The method of prevention and/or treatment of cancer according to the present invention has excellent cancer cell proliferation inhibition effect, and thus, it may be applied for various cancers, and specific examples of the cancer include uterine cancer, breast cancer, stomach cancer, brain cancer, rectal cancer, colorectal cancer, lung cancer, skin cancer, blood cancer and liver cancer, but not limited thereto.

In the method of prevention of cancer, for preferable salt forms of the active ingredients, preferable weight ratio of each active ingredient, and the like, those described relating to the pharmaceutical composition according to one embodiment of the invention may be applied.

The pharmaceutical composition of the present invention comprises at least one pharmaceutically acceptable carrier in addition to the active ingredient. As used herein, 'pharmaceutically acceptable carrier' means known pharmaceutical excipient that is useful for formulation of a pharmaceutically active compound for administration and is substantially non-toxic and non-sensitive under use conditions. The exact ratio of the excipient is determined by standard pharmaceutical practice, as well as by the solubility and the chemical properties of active compounds and the selected administration route.

The pharmaceutical composition of the present invention may be formulated into a form suitable for a desired administration method using adjuvant such as a physiologically acceptable excipient, a disintegrating agent, a sweetener, a binder, coating material, a blowing agent, a lubricant, a slip modifier, a flavoring agent and the like.

The pharmaceutical composition may be formulated in the form of tablets, capsules, pills, granule, powder, injections or liquid.

The dosage form of the pharmaceutical composition and the pharmaceutically acceptable carrier may be appropriately selected according to technologies known in the art, and for the principle of formulation of the pharmaceutical composition, various documents may be referred to.

Meanwhile, as used herein, a 'subject' means a warm-blooded animal such as a mammal with a specific disease, disorder or condition, and for example, it includes a human being, an orangutan, a chimpanzee, a mouse, a rat, a dog, a cow, a chicken, a pig, a goat, a sheep and the like, but is not limited thereto.

And, 'treatment' includes relieving symptoms, temporarily or permanently removing the cause of symptoms, or preventing or slowing the appearance of symptoms and the progress of the disease, disorder or condition, but is not limited thereto.

The effective amount of the active ingredient of the pharmaceutical composition of the present invention means an amount required for achieving treatment of a disease. Thus, it may be controlled according to various factors including kind of disease, severity of disease, kind and content of active ingredients and other ingredients contained in the composition, kind of dosage form, and age, weight, general health state, gender and diet of a patient, administration time, administration route, secretion rate of the composition, treatment period, simultaneously used drugs, and the like. For example, in the case of an adult, the compound of the Chemical Formula 1 may be administered once or several times a day in the total amount of 50 to 3000 mg/kg.

Advantageous Effects

The biguanide derivatives according to the present invention may exhibit excellent cancer cell proliferation inhibition and cancer metastasis and recurrence inhibition effects even with a small amount compared to the existing drugs, and thus, may be usefully used for treatment of various cancers including uterine cancer, breast cancer, stomach cancer, brain cancer, rectal cancer, colorectal cancer, lung cancer, skin cancer, blood cancer and liver cancer and the like, inhibition of cancer cell proliferation, and inhibition of cancer metastasis.

MODE FOR INVENTION

A better understanding of the present invention may be obtained through the following examples which are set forth to illustrate, but are not to be construed as the limit of the present invention.

Example 1: Preparation of N1-pyrrolidine-N5-(benzo[1,3]dioxol-5-ylmethyl) biguanide.HCl

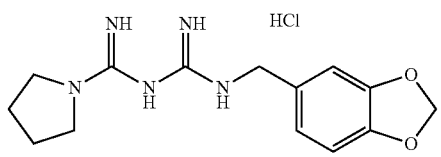 [SMILES: Cl ; N=C(NCc1ccc2c(c1)OCO2)NC(=N)N1CCCC1]

To a solution (20 mL) of piperonyl amine (0.8 ml, 6.58 mmol) dissolved in butanol was added by strong hydrochloric acid (0.6 mL, 6.58 mmol) at room temperature. The reaction mixture was added by N1-pyrrolidine cyanoguanidine (1.0 g, 7.24 mmol) and then stirred with reflux for 18 hr. The reaction mixture was concentrated under reduced pressure, separated and purified by a chromatography using MC:MeOH=9:1. The title compound was produced in white solid (1.5 g, 70%).

$^1$H NMR (400 MHz, CD$_3$OD) δ 6.94 (s, 1H), 6.83 (s, 2H), 5.98 (s, 2H), 4.31 (s, 2H), 3.55 (d, 4H), 1.51 (s, 4H) LC-MS m/z 290.2 [M+1]

Example 2: Preparation of N1-pyrrolidine-N5-(4-methoxy)phenyl biguanide.HCl

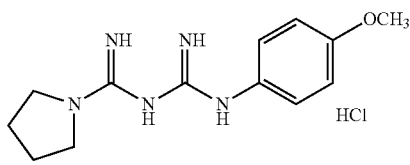 [SMILES: COc1ccc(NC(=N)NC(=N)N2CCCC2)cc1 ; Cl]

The title compound was produced according to the substantially same method as described in Example 1, except that 4-methoxy aniline was used instead of piperonyl amine.

$^1$H NMR (400 MHz, DMSO) δ 9.22 (bs, 1H), 7.39 (bs, 2H), 7.27 (d, J=8.8 Hz, 2H), 6.88 (d, J=8.8 Hz, 2H), 6.72 (bs, 2H), 3.37 (m, 4H), 1.98 (m, 4H), LC-MS m/z 262.2 [M+1]

Example 3: Preparation of N1-pyrrolidine-N5-(3-chloro-4-methoxy)phenyl biguanide.HCl

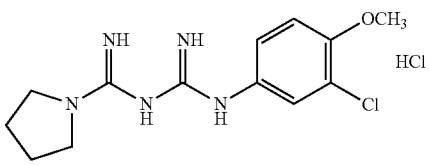 [SMILES: COc1ccc(NC(=N)NC(=N)N2CCCC2)cc1Cl ; Cl]

The title compound in a white solid was produced according to the substantially same method as described in Example 1, except that 3-chloro-4-methoxy aniline was used instead of piperonyl amine $^1$H NMR (400 MHz, DMSO) δ 9.22 (bs, 1H), 7.53 (d, J=2.4 Hz, 1H), 7.51 (bs, 2H), 7.25 (dd, J=8.8 Hz, 1H), 7.09 (d, J=8.8 Hz, 1H), 6.80 (bs, 2H), 3.37 (m, 4H), 1.90 (m, 4H), LC-MS m/z 296.1 [M+1]

Example 4: Preparation of N1-pyrrolidine-N5-(2,6-difluoro-N5-methyl)phenyl biguanide.HCl

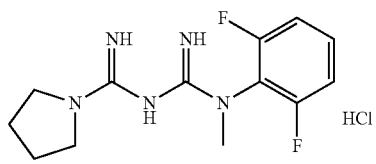 [SMILES: CN(C(=N)NC(=N)N1CCCC1)c1c(F)cccc1F ; Cl]

The title compound in a white solid was produced according to the substantially same method as described in Example 1, except that 2,6-difluoro N-methylaniline was used instead of piperonyl amine $^1$H NMR (600 MHz, CD$_3$OD) δ 6.42 (s, 1H), 7.10 (m, 2H), 3.36 (m, 4H), 3.28 (s, 3H), 1.93 (m, 4H) LC-MS m/z 282.1 [M+1]

Example 5: Preparation of N1-pyrrolidine-N5-(4-dimethylamino)phenyl biguanide.HCl

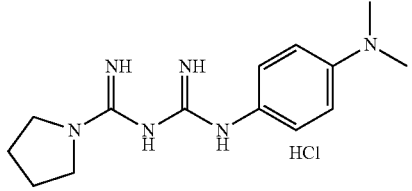 [SMILES: CN(C)c1ccc(NC(=N)NC(=N)N2CCCC2)cc1 ; Cl]

The title compound in a white solid was produced according to the substantially same method as described in Example 1, except that 4-dimethylamino aniline was used instead of piperonyl amine.

$^1$H NMR (600 MHz, CD$_3$OD) δ 7.15 (d, J=8.8 Hz, 2H), 6.77 (d, J=8.8 Hz, 2H), 3.41 (m, 4H), 2.91 (s, 6H), 1.95 (m, 4H) LC-MS m/z 275.2 [M+1]

Example 6: Preparation of N1-pyrrolidine-N5-(4-isopropyl)phenyl biguanide.HCl

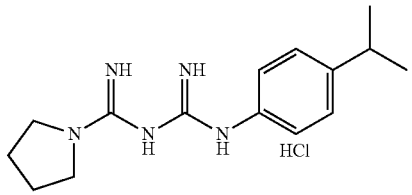 [SMILES: CC(C)c1ccc(NC(=N)NC(=N)N2CCCC2)cc1 ; Cl]

The title compound in a white solid was produced according to the substantially same method as described in Example 1, except that 4-isopropyl aniline was used instead of piperonyl amine.

$^1$H NMR (600 MHz, —CD$_3$OD) δ 7.27 (d, J=8.8 Hz, 2H), 7.20 (d, J=8.8 Hz, 2H), 3.48 (m, 4H), 2.90 (m, 1H), 2.03 (m, 4H), 1.24 (d, J=7.2 Hz, 6H), LC-MS m/z 274.2 [M+1]

Example 7: Preparation of N1-pyrrolidine-N5-(3-phenoxy)phenyl biguanide.HCl

The title compound in a white solid was produced according to the substantially same method as described in Example 1, except that 3-phenoxy aniline was used instead of piperonyl amine.

$^1$H NMR (600 MHz, CD$_3$OD) δ 7.37 (m, 2H), 7.26 (m, 2H), 7.21 (m, 1H), 7.14 (m, 1H), 7.01 (m, 3H), 6.72 (m, 4H), 2.03 (m, 4H) LC-MS m/z 346.1 [M+1]

Example 8: Preparation of N1-pyrrolidine-N5-(N-biphenyl-3-yl) biguanide.HCl

The title compound in a white solid was produced according to the substantially same method as described in Example 1, except that N-biphenyl-3-amine was used instead of piperonyl amine.

$^1$H NMR (400 MHz, CD$_3$OD) δ 7.63 (t, J=1.7 Hz, 1H), 7.59 (d, J=8.2 Hz, 2H), 7.38 (m, 6H) 3.51 (br d, 4H), 2.02 (Br d, 4H) LC-MS m/z 308.2 [M+1]

Example 9: Preparation of N1-pyrrolidine-N5-(N-biphenyl-4-yl) biguanide.HCl

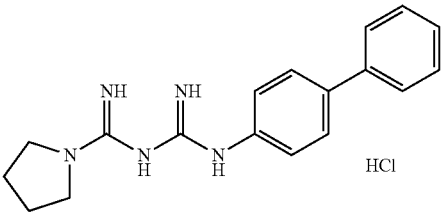 [SMILES: N=C(NC(=N)N1CCCC1)Nc1ccc(-c2ccccc2)cc1 ; Cl]

The title compound in a white solid was produced according to the substantially same method as described in Example 1, except that N-biphenyl-4-amine was used instead of piperonyl amine.

$^1$H NMR (400 MHz, CD$_3$OD) δ 7.60 (m, 4H), 7.47 (m, 4H), 7.31 (t, J=7.5 Hz, 1H), 3.52 (br d, J=41.8 Hz, 4H), 2.04 (br d, J=32.9 Hz, 4H) LC-MS m/z 308.2 [M+1]

Example 10: Preparation of N1-pyrrolidine-N5-(4'-fluorobiphenyl-3-yl) biguanide.HCl

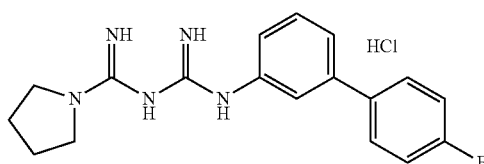

The title compound in a white solid was produced according to the substantially same method as described in Example 1, except that 4'-fluorobiphenyl-3-amine was used instead of piperonyl amine $^1$H NMR (400 MHz, CD$_3$OD) δ 7.61 (m, 3H), 7.33 (m, 3H), 7.17 (m, 2H), 3.48 (br d, J=37.9 Hz, 4H), 2.04 (br d, J=36.3 Hz, 4H) LC-MS m/z 326.2 [M+1]

Example 11: Preparation of N1-pyrrolidine-N5-(3'-fluorobiphenyl-4-yl) biguanide.HCl

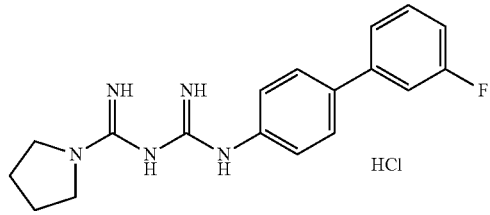 [SMILES: N=C(NC(=N)N1CCCC1)Nc1ccc(-c2cccc(F)c2)cc1 ; Cl]

The title compound in a white solid was produced according to the substantially same method as described in Example 1, except that 3'-fluorobiphenyl-4-amine was used instead of piperonyl amine $^1$H NMR (400 MHz, CD$_3$OD) δ 7.59 (d, J=6.6 Hz, 2H), 7.48 (m, 4H), 7.35 (d, J=9.4 Hz, 1H), 7.05 (m, 1H), 3.53 (br d, J=46.1 Hz, 4H), 2.04 (br d, J=34.4 Hz, 4H) LC-MS m/z 326.2 [M+1]

Example 12: Preparation of N1-pyrrolidine-N5-(4-fluoro)phenethyl biguanide.HCl

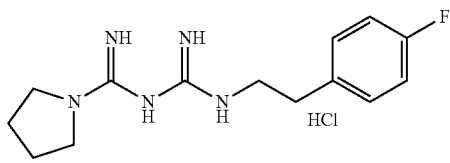 [SMILES: N=C(NCCc1ccc(F)cc1)NC(=N)N1CCCC1 ; Cl]

The title compound in a white solid was produced according to the substantially same method as described in Example 1, except that 4-fluorophenethyl amine was used instead of piperonyl amine.

$^1$H NMR (600 MHz, CD$_3$OD) δ 7.24 (m, 2H), 7.19 (m, 2H), 3.58 (m, 6H), 2.83 (t, J=7.2 Hz, 2H), 2.08 (m, 4H) LC-MS m/z 278.2 [M+1]

Example 13: Preparation of N1-pyrrolidine-N5-(2-phenylpropane-2-yl) biguanide.HCl

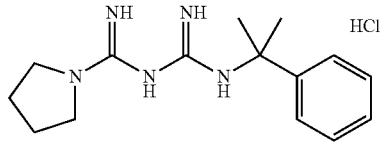 [SMILES: CC(C)(NC(=N)NC(=N)N1CCCC1)c1ccccc1 ; Cl]

The title compound in a white solid was produced according to the substantially same method as described in Example 1, except that 2-phenylpropane-2-amine was used instead of piperonyl amine.

$^1$H NMR (600 MHz, CD$_3$OD) δ 7.39(d, J=8.4 Hz, 2H), 7.3(t, J=8.4 Hz, 2H), 7.18 (t, J=8.4 Hz, 1H), 3.19 (m, 2H), 2.81 (m, 2H), 1.90 (m, 2H), 1.66 (s, 8H) LC-MS m/z 274.2 [M+1]

Example 14: Preparation of N1-pyrrolidine-N5-(5,6,7,8-tetrahydronaphthalene-2-yl) biguanide.HCl

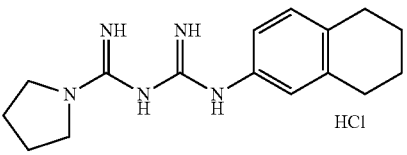 [SMILES: N=C(NC(=N)N1CCCC1)Nc1ccc2c(c1)CCCC2 ; Cl]

The title compound in a white solid was produced according to the substantially same method as described in Example 1, except that 5,6,7,8-tetrahydronaphthalene-2-amine was used instead of piperonyl amine.

$^1$H (600 MHz, CD$_3$OD) δ 7.03 (m, 3H), 3.48 (m, 4H), 2.73 (m, 4H), 2.02 (m, 4H), 1.79 (m, 4H) LC-MS m/z 286.2 [M+1]

Example 15: Preparation of N1-pyrrolidine-N5-(1,2,3,4-tetrahydronaphthalen-1-yl) biguanide.HCl

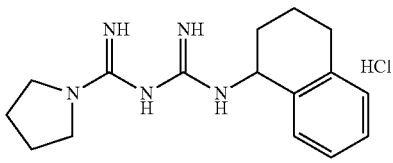 [SMILES: N=C(NC(=N)N1CCCC1)NC1CCCc2ccccc21 ; Cl]

The title compound in a white solid was produced according to the substantially same method as described in Example 1, except that 1,2,3,4-tetrahydronaphthalene-1-amine was used instead of piperonyl amine.

$^1$H NMR (600 MHz, CD$_3$OD) δ 7.33 (m, 1H), 7.15 (m, 2H), 7.10 (m, 1H), 5.03 (s, 1H), 3.46 (brs, 4H), 2.85 (m, 2H), 2.05~1.79 (m, 10H), LC-MS m/z 286.2 [M+1]

Example 16: Preparation of N1-(S)-2-methyl pyrrolidine-N5-(4-(trifluoromethoxy)phenyl biguanide.HCl

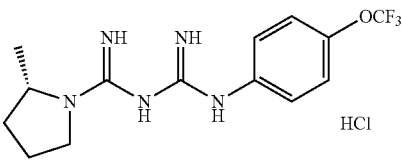 [SMILES: C[C@H]1CCCN1C(=N)NC(=N)Nc1ccc(OC(F)(F)F)cc1 ; Cl]

The title compound in a white solid was produced according to the substantially same method as described in Example 1, except that (S)-2-methyl pyrrolidine cyanoguanidine was used instead of pyrrolidine cyanoguanidine, and 4-(trifluoromethoxy)aniline was used instead of piperonyl amine.

$^1$H NMR (600 MHz, CD$_3$OD) δ 7.37 (m, 2H), 7.31 (m, 3H), 7.22 (d, J=9.0 Hz), 7.10 (t, J=7.2 Hz, 1H), 6.99 (m, 4H), 6.80 (dd, J=1.8 Hz, 1H) LC-MS m/z 330.1 [M+1]

Example 17: Preparation of N1-(S)-3-hydroxy pyrrolidine-N5-(4-trifluoromethoxy)phenyl biguanide.HCl

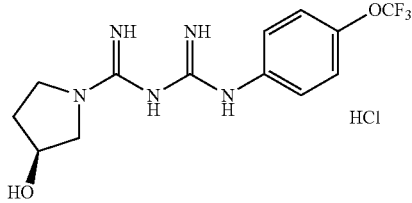 [SMILES: N=C(NC(=N)N1CC[C@H](O)C1)Nc1ccc(OC(F)(F)F)cc1 ; Cl]

The title compound in a white solid was produced according to the substantially same method as described in Example 1, except that (S)-3-hydroxy pyrrolidine cyanoguanidine was used instead of pyrrolidine cyanoguanidine, and 4-(trifluoromethoxy)aniline was used instead of piperonyl amine.

$^1$H NMR (600 MHz, CD$_3$OD) δ 7.47 (m, 2H), 7.22 (m, 2H), 4.42 (brs, 1H), 3.54 (m, 5H), 2.01 (m, 2H) LC-MS m/z 332.1 [M+1]

Example 18: Preparation of N1-4-hydroxy piperidine-N5-(4-trifluoromethoxy)phenyl biguanide.HCl

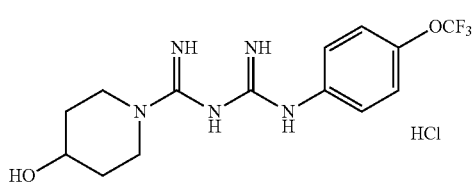 [SMILES: N=C(NC(=N)N1CCC(O)CC1)Nc1ccc(OC(F)(F)F)cc1 ; Cl]

To a solution (20 mL) of 4-trifluoromethoxyphenyl(0.77 ml, 4.76 mmol) dissolved in butanol was added by strong hydrochloric acid (0.40 mL, 4.76 mmol) at room temperature. The reaction mixture was added by 4-hydroxy piperidine cyanoguanine (0.3 g, 4.76 mmol) prepared by Reaction Scheme 1 and then stirred with reflux for 12 hr. The reaction mixture was concentrated under reduced pressure, and then was stirred with addition of ethyl acetate 20 ml for 2 hr. The obtained solid was filtrated, was washed with ethyl acetate, and dried under reduced pressure. The title compound was produced in white solid (54.8 mg, 8.2%).

$^1$H NMR (600 MHz, CD$_3$OD) δ 7.46 (m, 2H), 7.26 (d, J=8.4 Hz, 2H), 3.88 (m, 3H), 3.34 (m, 3H), 1.90 (m, 2H), 1.55 (m, 2H) LC-MS m/z 346.1 [M+1]

Example 19: Preparation of N1-(R)-3-hydroxy pyrrolidine-N5-(4-trifluoromethoxy)phenyl biguanide.HCl

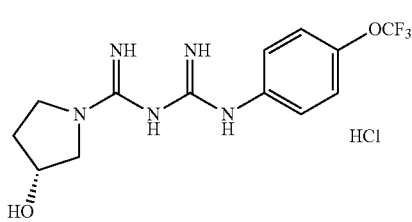 [SMILES: N=C(NC(=N)N1CC[C@@H](O)C1)Nc1ccc(OC(F)(F)F)cc1 ; Cl]

The title compound in a white solid was produced according to the substantially same method as described in Example 18, except that (R)-3-hydroxy pyrrolidine cyanoguanidine was used instead of 4-hydroxy piperidine.

$^1$H NMR (600 MHz, CD$_3$OD) δ 7.48 (d, J=9.0 Hz, 2H), 7.22 (d, J=9.0 Hz, 2H), 4.54 (brs, 1H), 3.55 (m, 4H), 1.07 (m, 2H) LC-MS m/z 332.1 [M+1]

Example 20: Preparation of N1-3-hydroxy methyl pyrrolidine-N5-(4-trifluoromethoxy)phenyl biguanide.HCl

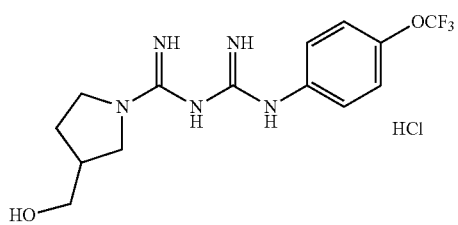 [SMILES: N=C(NC(=N)N1CCC(CO)C1)Nc1ccc(OC(F)(F)F)cc1 ; Cl]

The title compound in a white solid was produced according to the substantially same method as described in Example 18, except that 3-hydroxy methyl pyrrolidine cyanoguanidine was used instead of 4-hydroxy piperidine cyanoguanine.

$^1$H NMR (600 MHz, CD$_3$OD) δ 7.48 (m, 12H), 7.22 (m, 2H), 3.446 (m, 6H), 3.19 (m, 1H), 2.56 (m, 1H), 1.93 (m, 2H) LC-MS m/z 346.1 [M+1]

Example 21: Preparation of N1-4-hydroxy piperidine-N5-(4-phenoxy)phenyl biguanide.HCl

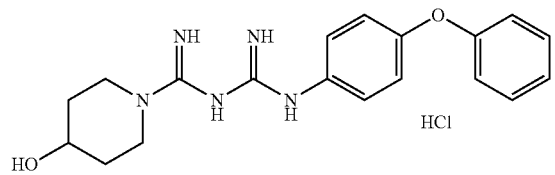 [SMILES: N=C(NC(=N)N1CCC(O)CC1)Nc1ccc(Oc2ccccc2)cc1 ; Cl]

The title compound in a white solid was produced according to the substantially same method as described in Example 18, except that 4-phenoxyphenyl aniline was used instead of 4-trifluoromethoxy phenyl.

$^1$H NMR (600 MHz, CD$_3$OD) δ 7.33 (m, 4H), 7.09 (m, 1H), 6.96 (m, 4H), 3.85 (m, 3H), 3.27 (m, 3H), 1.88 (m, 2H), 1.50 (m, 2H) LC-MS m/z 354.2 [M+1]

Example 22: Preparation of N1-4-hydroxy piperidine-N5-(3-phenoxy)phenyl biguanide.HCl

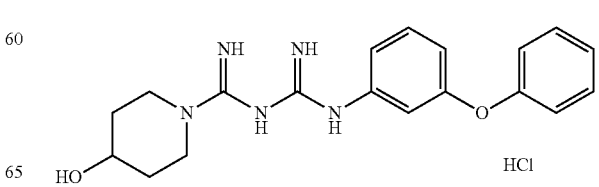

The title compound in a white solid was produced according to the substantially same method as described in Example 18, except that 4-phenoxyphenyl aniline was used instead of 4-trifluoromethoxy phenyl.

$^1$H NMR (600 MHz, CD$_3$OD) δ 7.35 (t, J=7.8 Hz, 2H), 7.26 (t, J=7.8 Hz, 1H), 7.16 (m, 1H), 7.12 (t, J=7.2 Hz, 1H), 7.00 (m, 3H), 6.72 (m, 1H), 3.86 (m, 3H), 3.27 (m, 3H), 1.88 (m, 2H), 1.52(m, 2H) LC-MS m/z 354.2 [M+1]

Example 23: Preparation of N1-pyrrolidine-N5-4-benzamide biguanide.HCl

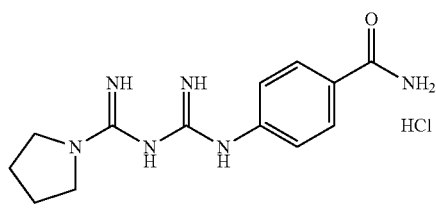 [SMILES: N=C(NC(=N)N1CCCC1)Nc1ccc(C(N)=O)cc1 ; Cl]

The title compound in a white solid was produced according to the substantially same method as described in Example 18, except that pyrrolidine cyanoguanidine was used instead of 4-hydroxy piperidine cyanoguanidine, 4-benzamide aniline was used instead of 4-trifluoromethoxy phenyl.

$^1$H NMR (400 MHz, DMSO-d6) δ 9.67 (s, 1H), 7.82 (s, 1H), 7.80 (d, J=8.8 Hz, 2H), 7.62 (s, 1H), 7.47 (d, J=8.8 Hz, 2H), 7.23 (s, 1H), 6.58 (s, 2H), 3.36 (m, 4H), 1.93 (m, 4H) LC-MS m/z 275.2 [M+1]

Example 24: Preparation of (E)-N—(N-(4-(3-oxo-3-(piperidin-1-yl)prop-1-enyl)phenyl)carbamimidoyl) pyrrolidine-1-carboximidamide.HCl

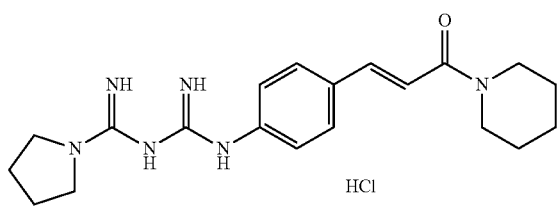 [SMILES: N=C(NC(=N)N1CCCC1)Nc1ccc(/C=C/C(=O)N2CCCCC2)cc1 ; Cl]

The title compound in a white solid was produced according to the substantially same method as described in Example 18, except that pyrrolidine cyanoguanidine was used instead of 4-hydroxy piperidine, and (E)-3-(4-aminophenyl)-1-(piperidin-1-yl)prop-2-en-1-on was used instead of 4-trifluoromethoxy aniline.

$^1$H NMR (600 MHz, DMSO-d6) δ 7.62 (d, J=8.4 Hz, 2H), 7.44 (d, J=8.4 Hz, 2H), 7.41 (d, J=15.6 Hz, 1H), 7.13 (d, J=15.6 Hz, 1H), 3.62 (m, 8H), 1.94 (m, 4H), 1.61 (m, 6H) LC-MS m/z 369.2 [M+1]

Example 25: Preparation of N—(N-(4-(piperidine-1-carbonyl)benzyl)carbamimidoyl)pyrrolidine-1-carboximidamide.HCl

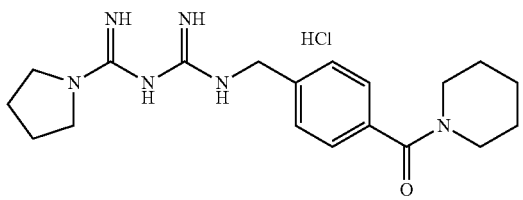 [SMILES: N=C(NCc1ccc(C(=O)N2CCCCC2)cc1)NC(=N)N1CCCC1 ; Cl]

The title compound in a white solid was produced according to the substantially same method as described in Example 18, except that pyrrolidine cyanoguanidine was used instead of 4-hydroxy piperidine, and (4-aminomethyl)phenyl)(piperidin-1-yl)methanone was used instead of 4-trifluoromethoxy aniline.

$^1$H NMR (600 MHz, CD$_3$OD) δ 7.43 (d, J=7.8 Hz, 2H), 7.37 (d, J=7.8 Hz, 2H), 4.57 (s, 2H), 3.59 (m, 8H), 2.04(m, 4H), 1.72 (m, 6H) LC-MS m/z 368.2 [M+2]

Example 26: Preparation of N—(N-(4-(3-oxo-3-(piperidin-1-yl)propyl)phenyl)carbamimidoyl)pyrrolidine-1-carboximidamide.HCl

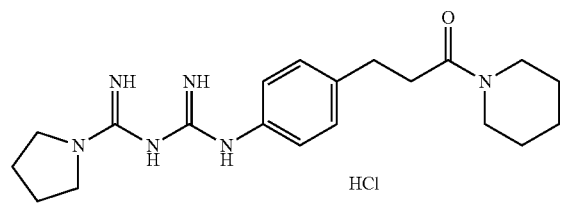 [SMILES: N=C(NC(=N)N1CCCC1)Nc1ccc(CCC(=O)N2CCCCC2)cc1 ; Cl]

The title compound in a white solid was produced according to the substantially same method as described in Example 18, except that pyrrolidine cyanoguanidine was used instead of 4-hydroxy piperidine, and (E)-3-(4-aminophenyl)-1-(piperidin-1-yl)propyl-1-on was used instead of 4-trifluoromethoxy aniline.

$^1$H NMR (600 MHz, CD$_3$OD) δ 7.30 (d, J=8.8 Hz, 2H), 7.20 (d, J=8.8 Hz, 2H), 3.52 (m, 8H), 2.89 (t, J=7.2 Hz, 2H), 2.68(t, J=7.2 Hz, 2H), 2.05 (m, 4H), 1.61 (m, 6H) LC-MS m/z 371.3 [M+1]

Example 27: Preparation of N-ethyl-4-((3-(imino(pyrrolidin-1-yl)methyl)guanidino)methyl)benzamide.HCl

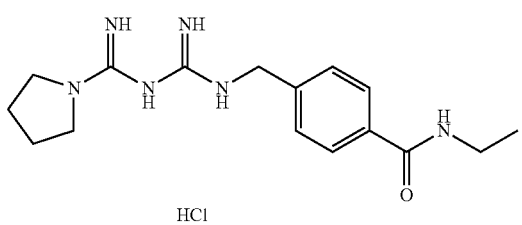 [SMILES: CCNC(=O)c1ccc(CNC(=N)NC(=N)N2CCCC2)cc1 ; Cl]

The title compound in a white solid was produced according to the substantially same method as described in Example 18, except that pyrrolidine cyanoguanidine was used instead of 4-hydroxy piperidine, and 4-(aminomethyl)-N-ethylbenzamide was used instead of 4-trifluoromethoxy aniline.

$^1$H NMR (600 MHz, CD$_3$OD) δ 7.77 (d, J=12 Hz, 2H), 7.397 (d, J=18 Hz, 2H), 4.46(s, 2H), 3.36 (m, 6H), 1.93 (m, 4H), 1.21 (t, J=12 Hz, 3H) LC-MS m/z 317.2 [M+1]

Example 28: Preparation of N—(N-(4-(2-oxo-2-(piperidin-1-yl)ethylthio)phenyl)carbamimidoyl)pyrrolidine-1-carboximidamide.HCl

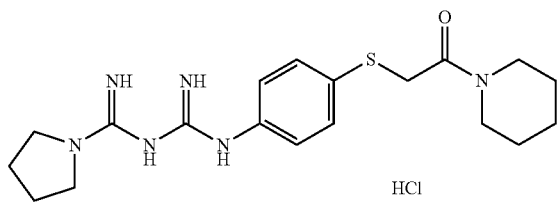 [SMILES: N=C(NC(=N)N1CCCC1)Nc1ccc(SCC(=O)N2CCCCC2)cc1 ; Cl]

The title compound in a white solid was produced according to the substantially same method as described in Example 18, except that pyrrolidine cyanoguanidine was used instead of 4-hydroxy piperidine, and 2-(4-aminophenyl thio)-1-(piperidin-1-yl)ethanone was used instead of 4-trifluoromethoxy aniline.

$^1$H NMR (600 MHz, CD$_3$OD) δ 7.40 (d, J=18 Hz, 2H), 7.32 (d, J=18 Hz, 2H), 3.75 (s, 2H), 3.49 (m, 8H), 1.95 (m, 4H), 1.51 (m, 4H) LC-MS m/z 389.2 [M+1]

Example 29: Preparation of (S)-3-hydroxy-N—(N-(4-(2-oxo-2-(piperidin-1-yl)ethylthio)phenyl)carbamimidoyl)pyrrolidine-1-carboximidamide.HCl

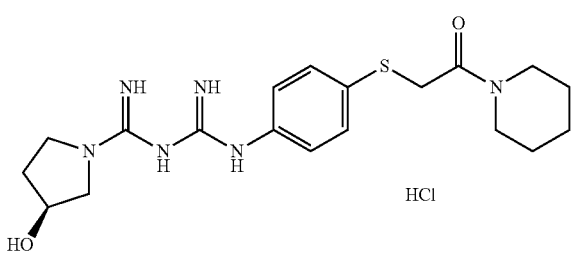 [SMILES: N=C(NC(=N)N1CC[C@H](O)C1)Nc1ccc(SCC(=O)N2CCCCC2)cc1 ; Cl]

The title compound in a white solid was produced according to the substantially same method as described in Example 18, except that (S)-2-hydroxy pyrrolidine cyanoguanidine was used instead of 4-hydroxy piperidine, and 2-(4-aminophenyl thio)-1-(piperidin-1-yl)ethanone was used instead of 4-trifluoromethoxy aniline.

$^1$H NMR (600 MHz, CD$_3$OD) δ 7.40 (d, J=18 Hz, 2H), 7.32 (d, J=18 Hz, 2H), 4.58 (brs, 1H), 3.75(s, 2H), 3.51 (m, 3H), 2.06(m. 2H), 1.63 (m, 5H) LC-MS m/z 405.2 [M+1]

Example 30: Preparation of N-ethyl-3-((3-(imino(pyrrolidin-1-yl)methyl)guanidino)methyl)benzamide.HCl

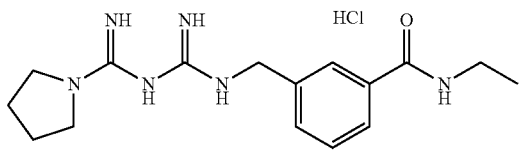 [SMILES: Cl ; CCNC(=O)c1cccc(CNC(=N)NC(=N)N2CCCC2)c1]

The title compound in a white solid was produced according to the substantially same method as described in Example 18, except that pyrrolidine cyanoguanidine was used instead of 4-hydroxy piperidine, and 3-(aminomethyl)-N-ethylbenzamide was used instead of 4-trifluoromethoxy aniline.

$^1$H NMR (600 MHz, CD$_3$OD) δ 7.83 (m, 1H), 7.69 (d, J=7.8 Hz, 1H), 7.49 (d, J=7.8 Hz, 1H), 7.42(t, J=7.8 Hz, 1H), 4.47 (s, 2H), 3.41 (m, 4H), 3.37(t, J=6.0 Hz, 2H), 1.95 (m, 4H), 1.21 (m, 3H) LC-MS m/z 317.2 [M+1]

Example 31: Preparation of N1-4-methyl piperazine-N5-(4-bromo)phenyl biguanide.HCl

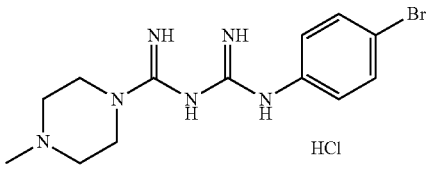 [SMILES: CN1CCN(C(=N)NC(=N)Nc2ccc(Br)cc2)CC1 ; Cl]

To a solution (10 mL) of 4-bromo aniline (154 mg, 0.897 mmol) dissolved in butanol was added by strong hydrochloric acid (0.11 mL, 0.897 mmol) at room temperature. The reaction mixture was added by methyl piperazine cyanoguanidine (150 mg, 0.897 mmol) and then stirred with reflux for 18 hr. The reaction mixture was concentrated under reduced pressure, and then was separated and purified by a chromatography using MC:MeOH=9:1. The title compound was produced in white solid phase (90.2 mg, 27%).

$^1$H NMR (600 MHz, CD$_3$OD) δ 7.47 (m, 2H), 7.29 (m, 2H), 3.58 (m, 4H), 2.51 (m, 4H), 2.35 (s, 3H); LC-MS m/z 340.0 [M+1]+; mp 227~229° C.

Example 32: Preparation of N1-4-methyl piperazine-N5-(3-bromo)phenyl biguanide.HCl

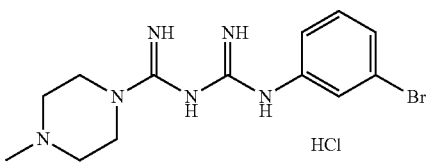 [SMILES: CN1CCN(C(=N)NC(=N)Nc2cccc(Br)c2)CC1 ; Cl]

The title compound in a white solid was produced according to the substantially same method as described in Example 31, except that 3-bromo aniline was used instead of 4-bromo aniline.

¹H NMR (600 MHz, CD₃OD) δ 7.44 (m, 1H), 7.05 (m, 3H), 3.39 (m, 3H), 2.31 (m, 3H), 2.14 (s, 3H); LC-MS m/z 340.4 [M+1]+; mp 228~229° C.

Example 33: Preparation of N1-4-methyl piperazine-N5-(2-bromo)phenyl biguanide.HCl

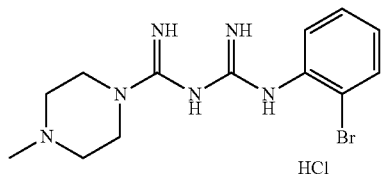 [SMILES: CN1CCN(C(=N)NC(=N)Nc2ccccc2Br)CC1 ; Cl]

The title compound in a white solid was produced according to the substantially same method as described in Example 31, except that 2-bromo aniline was used instead of 4-bromo aniline.

¹H NMR (600 MHz, CD₃OD) δ 7.44 (m, 1H), 7.37 (m, 1H), 7.15 (m, 1H), 6.93 (m, 1H), 3.31 (m, 4H), 2.26 (m, 4H), 2.11 (s, 3H); LC-MS m/z 340.4 [M+1]+; mp 161~163° C.

Example 34: Preparation of N1-4-methyl piperazine-N5-(3-bromo)benzyl biguanide.HCl

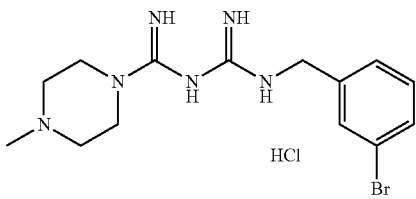 [SMILES: CN1CCN(C(=N)NC(=N)NCc2cccc(Br)c2)CC1 ; Cl]

The title compound in a white solid was produced according to the substantially same method as described in Example 31, except that 3-bromobenzyl amine was used instead of 4-bromo aniline.

¹H NMR (600 MHz, CD₃OD) δ 7.56 (m, 1H), 7.35 (m, 2H) 7.18 (m, 1H), 4.49 (m, 2H), 3.46 (m, 4H), 2.42 (m, 4H), 2.29 (s, 3H); LC-MS m/z 354.4 [M+1]+; mp 216~218° C.

Example 35: Preparation of N1-4-methyl piperazine-N5-(4-fluoro-3-trifluoromethyl)phenyl biguanide.HCl

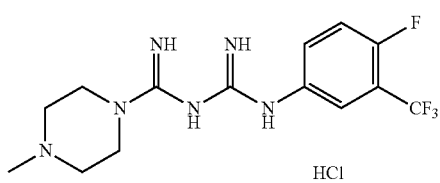 [SMILES: CN1CCN(C(=N)NC(=N)Nc2ccc(F)c(C(F)(F)F)c2)CC1 ; Cl]

The title compound in a white solid was produced according to the substantially same method as described in Example 31, except that 4-fluoro-3-trifluoromethyl aniline was used instead of 4-bromo aniline.

¹H NMR (600 MHz, CD₃OD) δ 7.78 (m, 1H), 7.58 (m, 1H), 7.30 (m, 1H), 3.57 (m, 4H), 2.49 (m, 4H), 2.34 (s, 3H); LC-MS m/z 347.2 [M+1]+; mp 254~256° C.

Example 36: Preparation of N1-4-methyl piperazine-N5-(3-chloro-4-trifluoromethoxy)phenyl biguanide.HCl

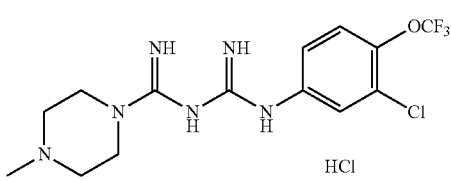 [SMILES: CN1CCN(C(=N)NC(=N)Nc2ccc(OC(F)(F)F)c(Cl)c2)CC1 ; Cl]

The title compound in a white solid was produced according to the substantially same method as described in Example 31, except that 3-chloro-4-trifluoromethoxy aniline was used instead of 4-bromo aniline.

¹H NMR (600 MHz, CD₃OD) δ 7.72 (m, 1H), 7.37 (m, 2H), 3.60 (m, 4H), 2.53 (m, 4H), 2.35 (s, 3H); LC-MS m/z 379.4 [M+1]+; mp 229~231° C.

Example 37: Preparation of N1-4-methyl piperazine-N5-(3-fluoro-4-trifluoromethoxy)phenyl biguanide.HCl

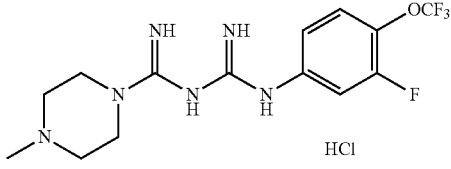 [SMILES: CN1CCN(C(=N)NC(=N)Nc2ccc(OC(F)(F)F)c(F)c2)CC1 ; Cl]

The title compound in a white solid was produced according to the substantially same method as described in Example 31, except that 3-fluoro-4-trifluoromethoxy aniline was used instead of 4-bromo aniline.

¹H NMR (600 MHz, CD₃OD) δ 7.71 (m, 1H), 7.50 (m, 1H), 7.29 (m, 1H), 3.61 (m, 4H), 2.53 (m, 4H), 2.36 (s, 3H); LC-MS m/z 363.5 [M+1]+; mp 230~232° C.

Example 38: Preparation of N1-4-methyl piperazine-N5-(4-chloro-3-trifluoromethyl)phenyl biguanide.HCl

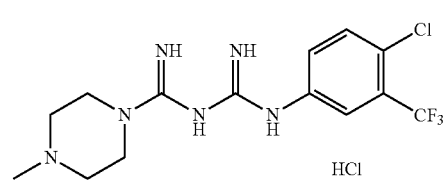 [SMILES: CN1CCN(C(=N)NC(=N)Nc2ccc(Cl)c(C(F)(F)F)c2)CC1 ; Cl]

The title compound in a white solid was produced according to the substantially same method as described in Example 31, except that 4-chloro-3-trifluoromethyl aniline was used instead of 4-bromo aniline.

¹H NMR (600 MHz, CD₃OD) δ 7.89 (m, 1H), 7.57 (m, 2H), 3.56 (m, 4H), 2.82 (m, 4H), 2.55 (s, 3H); LC-MS m/z 363.5 [M+1]+; mp 231~233° C.

Example 39: Preparation of N1-4-methyl piperazine-N5-(4-chloro-3-trifluoromethoxy)phenyl biguanide.HCl

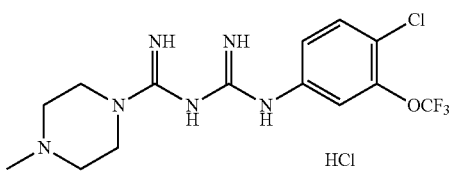 [SMILES: CN1CCN(C(=N)NC(=N)Nc2ccc(Cl)c(OC(F)(F)F)c2)CC1 ; Cl]

The title compound in a white solid was produced according to the substantially same method as described in Example 31, except that 4-chloro-3-trifluoromethoxy aniline was used instead of 4-bromo aniline.

¹H NMR (600 MHz, CD₃OD) δ 7.55 (m, 1H), 7.49 (m, 1H), 7.31 (m, 1H), 4.33 (m, 2H), 3.49 (m, 2H), 3.44 (m, 2H), 3.23 (m, 2H), 2.93 (s, 3H); LC-MS m/z 379.2 [M+1]+; mp 180~182° C.

Example 40: Preparation of N1-4-methyl piperazine-N5-(4-fluoro-3-trifluoromethoxy)phenyl biguanide.HCl

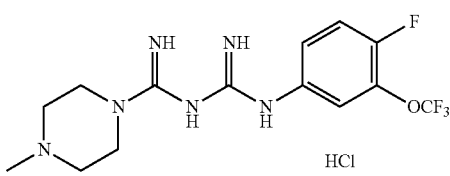 [SMILES: CN1CCN(C(=N)NC(=N)Nc2ccc(F)c(OC(F)(F)F)c2)CC1 ; Cl]

The title compound in a white solid was produced according to the substantially same method as described in Example 31, except that 4-fluoro-3-trifluoromethoxy aniline was used instead of 4-bromo aniline.

¹H NMR (600 MHz, CD₃OD) δ 7.62 (m, 1H), 7.29 (m, 2H), 4.49 (s, 2H), 3.56 (m, 4H), 2.88 (m, 4H), 2.71 (s, 3H); LC-MS m/z 363.2 [M+1]+; mp 216~218° C.

Example 41: Preparation of N1-4-methyl piperazine-N5-(4-fluoro-3-trifluoromethoxy)benzyl biguanide.HCl

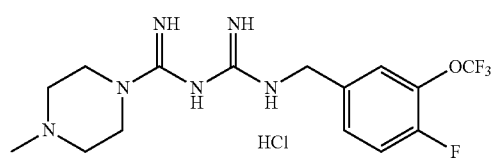 [SMILES: CN1CCN(C(=N)NC(=N)NCc2ccc(F)c(OC(F)(F)F)c2)CC1 ; Cl]

The title compound in a white solid was produced according to the substantially same method as described in Example 31, except that 4-fluoro-3-trifluoromethyl benzyl amine was used instead of 4-bromo aniline.

¹H NMR (600 MHz, CD₃OD) δ 7.34 (m, 3H), 4.40 (s, 2H), 3.52 (m, 4H), 2.52 (m, 4H), 3.37 (s, 3H); LC-MS m/z 377.2 [M+1]+; mp 222~224° C.

Example 42: Preparation of N1-4-methyl piperazine-N5-(3-fluoro-4-trifluoromethyl)benzyl biguanide.HCl

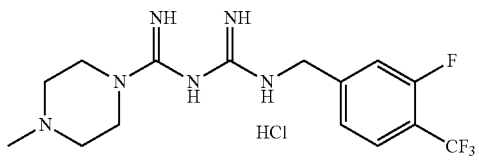 [SMILES: CN1CCN(C(=N)NC(=N)NCc2ccc(C(F)(F)F)c(F)c2)CC1 ; Cl]

The title compound in a white solid was produced according to the substantially same method as described in Example 31, except that 3-fluoro-4-trifluoromethyl benzyl amine was used instead of 4-bromo aniline.

¹H NMR (600 MHz, CD₃OD) δ 7.64 (m, 1H), 7.28 (m, 2H), 4.49 (s, 2H), 3.66 (m, 4H), 3.02 (m, 4H), 2.67 (s, 3H); LC-MS m/z 361.2 [M+1]+; mp 225~227° C.

Example 43: Preparation of N1-4-methyl piperazine-N5-(3-fluoro-4-trifluoromethoxy)benzyl biguanide.HCl

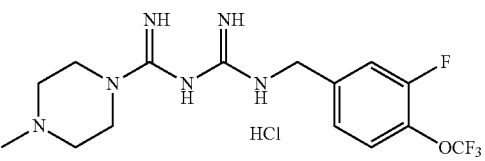 [SMILES: CN1CCN(C(=N)NC(=N)NCc2ccc(OC(F)(F)F)c(F)c2)CC1 ; Cl]

The title compound in a white solid was produced according to the substantially same method as described in Example 31, except that 3-fluoro-4-trifluoromethoxy benzyl amine was used instead of 4-bromo aniline.

¹H NMR (600 MHz, CD₃OD) δ 7.36 (m, 3H), 4.42 (s, 2H), 3.53 (m, 4H), 2.52 (m, 4H), 2.38 (s, 3H); LC-MS m/z 377.2 [M+1]+; mp 221~223° C.

Example 44: Preparation of N1-4-methyl piperazine-N5-(3-fluoro-4-trifluoromethyl)phenyl biguanide.HCl

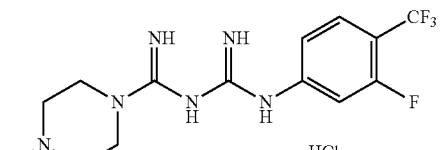

The title compound in a white solid was produced according to the substantially same method as described in Example 31, except that 3-fluoro-4-trifluoromethyl benzyl amine was used instead of 4-bromo aniline.

¹H NMR (600 MHz, CD₃OD) δ 7.59 (m, 2H), 7.26 (m, 1H), 3.62 (m, 4H), 2.53 (m, 4H), 2.34 (s, 3H); LC-MS m/z 347.2 [M+1]+; mp 224~226° C.

Example 45: Preparation of N1-4-ethyl piperazine-N5-(4-trifluoromethoxy)phenyl biguanide.HCl

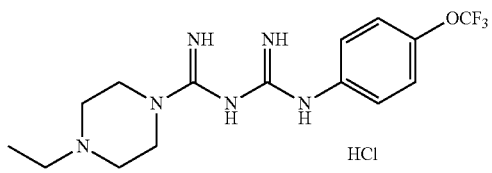 [SMILES: CCN1CCN(C(=N)NC(=N)Nc2ccc(OC(F)(F)F)cc2)CC1 ; Cl]

The title compound in a white solid was produced according to the substantially same method as described in Example 31, except that ethyl piperazine cyanoguanidine was used instead of methyl piperazine cyanoguanidine, and 3-trifluoromethoxy aniline was used instead of 4-bromo aniline.

$^1$H NMR (600 MHz, CD$_3$OD) δ 7.44 (m, 2H), 7.23 (m, 2H), 3.59 (m, 4H), 3.17 (m, 1H), 2.56 (m, 4H), 2.49 (m, 1H) 1.12 (m, 3H); LC-MS m/z 359.2 [M+1]+; mp 242~244° C.

Example 46: Preparation of N1-(2R,6S)-2,6-dimethyl piperidine-N5-(4-(2-aminoethyl)phenyl biguanide.HCl

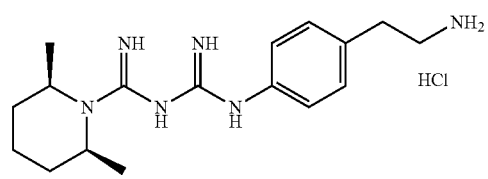 [SMILES: C[C@@H]1CCC[C@H](C)N1C(=N)NC(=N)Nc1ccc(CCN)cc1 ; Cl]

The title compound in a white solid was produced according to the substantially same method as described in Example 31, except that 2,6-dimethyl piperidine was used instead of methyl piperazine cyanoguanidine, and cyanoguanidine, 4-(2-aminoethyl) aniline was used instead of 4-bromo aniline.

$^1$H NMR (600 MHz, CD$_3$OD) δ 7.38 (d, 2H), 7.25 (d, 2H), 4.60~4.40 (s, 2H), 3.16 (t, 2H), 2.94 (t, 2H), 1.90~1.51 (m, 6H) 1.30 (s, 6H); LC-MS m/z 317.3 [M+1]; mp 230~235° C.

Example 47: Preparation of N1-pyrrolidine-N5-(4-(2-aminoethyl)phenyl biguanide.HCl

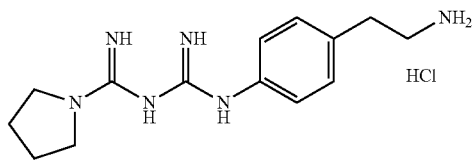 [SMILES: N=C(NC(=N)N1CCCC1)Nc1ccc(CCN)cc1 ; Cl]

The title compound in a white solid was produced according to the substantially same method as described in Example 31, except that pyrrolidine cyano was used instead of methyl piperazine cyanoguanidine, and guanidine, 4-(2-aminoethyl)aniline was used instead of 4-bromo aniline.

$^1$H NMR (600 MHz, CD$_3$OD) δ 7.39 (d, 2H), 7.25 (d, 2H), 3.48 (d, 4H), 3.16 (t, 2H), 2.94 (t, 2H), 2.05 (d, 4H); LC-MS m/z 275.2 [M+1]; mp 230~235° C.

Example 48: Preparation of N1-2-methyl piperidine-N5-(4-(2-aminoethyl)phenyl biguanide.HCl

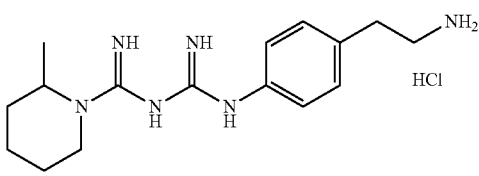 [SMILES: CC1CCCCN1C(=N)NC(=N)Nc1ccc(CCN)cc1 ; Cl]

The title compound in a white solid was produced according to the substantially same method as described in Example 31, except that 2-methyl piperidine cyanoguanidine was used instead of methyl piperazine cyanoguanidine, and 4-(2-aminoethyl)aniline was used instead of 4-bromo aniline.

$^1$H NMR (600 MHz, CD$_3$OD) δ 7.37 (d, 2H), 7.27 (d, 2H), 4.41 (s, 1H), 3.95 (d, 1H), 3.16 (m, 2H), 3.11 (m, 1H), 2.90 (m, 2H), 1.75~1.50 (m, 6H), 1.26 (d, 3H); LC-MS m/z 303.3 [M+1]; mp 230~235° C.

Example 49: Preparation of N1-3,5-dimethyl piperidine-N5-(4-(2-aminoethyl)phenyl biguanide.HCl

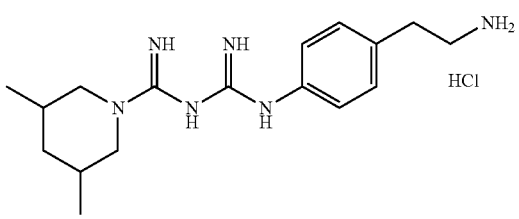 [SMILES: CC1CC(C)CN(C(=N)NC(=N)Nc2ccc(CCN)cc2)C1 ; Cl]

The title compound in a white solid was produced according to the substantially same method as described in Example 31, except that 3,5-dimethyl piperidine cyanoguanidine was used instead of methyl piperazine cyanoguanidine, and 4-(2-aminoethyl)aniline was used instead of 4-bromo aniline.

$^1$H NMR (600 MHz, CD$_3$OD) δ 7.36 (d, 2H), 7.26 (d, 2H), 4.03 (s, 2H), 3.16 (t, 2H), 2.9 (t, 2H), 2.46 (t, 2H), 1.87 (d, 1H), 1.68 (m, 2H), 0.94 (d, 6H), 0.88 (m, 1H); LC-MS m/z 317.3 [M+1]; mp 230~235° C.

Example 50: Preparation of N1-3-methyl piperidine-N5-(4-(2-aminoethyl)phenyl biguanide.HCl

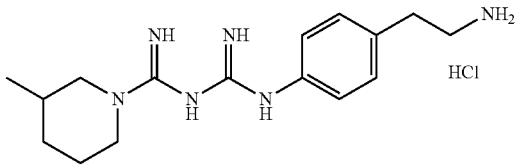 [SMILES: CC1CCCN(C(=N)NC(=N)Nc2ccc(CCN)cc2)C1 ; Cl]

The title compound in a white solid was produced according to the substantially same method as described in Example 31, except that 3-methyl piperidine cyanoguanidine was used instead of methyl piperazine cyanoguanidine, and 4-(2-aminoethyl)aniline was used instead of 4-bromo aniline.

¹H NMR (600 MHz, CD₃OD) δ 7.37 (d, 2H), 7.26 (d, 2H), 3.96 (dd, 2H), 3.16 (t, 2H), 2.99 (m, 1H), 2.94 (t, 2H), 2.67 (t, 1H), 1.86 (m, 1H), 1.74 (m, 1H), 1.67 (m, 1H), 1.57 (m, 1H), 0.94 (d, 3H); LC-MS m/z 303.2 [M+1]+; mp 230~235° C.

Example 51: Preparation of N1-3,3-difluoro pyrrolidine-N5-(4-trifluoromethoxy)phenyl biguanide.HCl

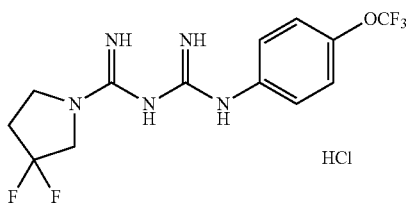 [SMILES: N=C(NC(=N)N1CCC(F)(F)C1)Nc1ccc(OC(F)(F)F)cc1 ; Cl]

The title compound in a white solid was produced according to the substantially same method as described in Example 31, except that 3,3-difluoro pyrrolidinecyanoguanidine was used instead of methyl piperazine cyanoguanidine, and 4-(trifluoromethoxy)aniline was used instead of 4-bromo aniline.

¹H NMR (600 MHz, CD₃OD) δ 7.45 (d, J=9.0 Hz, 2H), 7.26 (d, J=8.4 Hz, 2H), 3.82 (t, J=12.6 Hz, 2H), 3.70 (t, J=6.6 Hz, 2H), 2.51 (s, 2H) LC-MS m/z 352.2 [M+1]

Example 52: Preparation of N1-4,4-difluoro piperidine-N5-(4-trifluoromethoxy)phenyl biguanide.HCl

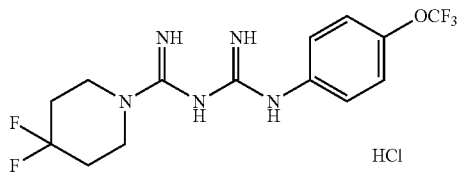 [SMILES: N=C(NC(=N)N1CCC(F)(F)CC1)Nc1ccc(OC(F)(F)F)cc1 ; Cl]

The title compound in a white solid was produced according to the substantially same method as described in Example 31, except that 4,4-difluoro piperidine cyanoguanidine was used instead of methyl piperazine cyanoguanidine, and 4-(trifluoromethoxy)aniline was used instead of 4-bromo aniline.

¹H NMR (600 MHz, CD₃OD) δ 7.43 (d, J=9.0 Hz, 2H), 7.25 (d, J=7.8 Hz, 2H), 3.68 (t, J=6.0 Hz, 4H), 2.06 (m, 4H) LC-MS m/z 366.2 [M+1]

Example 53: Preparation of N1-4-(methylsulfonyl)piperidine-N5-(4-trifluoromethoxy)phenyl biguanide.HCl

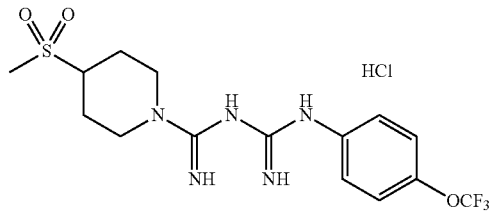 [SMILES: CS(=O)(=O)C1CCN(C(=N)NC(=N)Nc2ccc(OC(F)(F)F)cc2)CC1 ; Cl]

The title compound in a white solid was produced according to the substantially same method as described in Example 31, except that 4-methyl sulfonyl piperidine cyanoguanidine was used instead of methyl piperazine cyanoguanidine, and 4-(trifluoromethoxy)aniline was used instead of 4-bromo aniline.

¹H NMR (600 MHz, CD₃OD) 7.45 (d, J=9.0 Hz, 2H), 7.25 (d, J=7.8 Hz, 2H), 4.26 (d, J=13.8 Hz, 2H), 3.42 (m, 2H), 3.09 (t, J=12.0 Hz, 2H), 2.20 (d, J=10.8 Hz, 2H), 1.82 (m, 3H) LC-MS m/z 408.1 [M+1]

Example 54: Preparation of N5-(2,4-(dichloro)phenyl biguanide.HCl

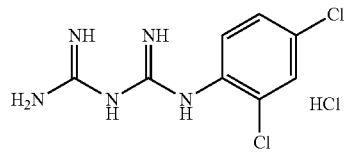 [SMILES: N=C(N)NC(=N)Nc1ccc(Cl)cc1Cl ; Cl]

To a solution (20 mL) of 2,4-dichloro aniline (0.64 g, 3.92 mmol) dissolved in butanol was added by strong hydrochloric acid (0.31 mL, 3.57 mmol) at room temperature. The reaction mixture was added by dicyandiamide (0.3 g, 3.57 mmol) and then stirred with reflux for 2 hr. The reaction mixture was concentrated under reduced pressure, and then stirred with addition of ethyl acetate 20 ml for 2 hr. The obtained solid was filtrated, was washed with ethyl acetate, and dried under reduced pressure. The title compound was produced in white solid phase (0.5 g, 54%).

¹H NMR (600 MHz, CD₃OD) δ 7.50 (d, 1H), 7.31 (d, 2H); LC-MS m/z 246.1 [M]+; mp 230~235° C.

Example 55: Preparation of N5-4-fluorophenyl biguanide.HCl

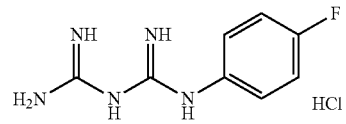 [SMILES: N=C(N)NC(=N)Nc1ccc(F)cc1 ; Cl]

The title compound in a white solid was produced according to the substantially same method as described in Example 54, except that 4-fluoroaniline was used instead of 2,4-dichloro aniline.

¹H NMR (600 MHz, CD₃OD) δ 7.36 (d, 2H), 7.08 (d, 2H); LC-MS m/z 196.2 [M+1]+; mp 230~235° C.

Example 56: Preparation of N5-(3,4-(dichloro)phenyl biguanide.HCl

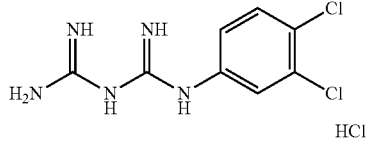 [SMILES: N=C(N)NC(=N)Nc1ccc(Cl)c(Cl)c1 ; Cl]

The title compound in a white solid was produced according to the substantially same method as described in Example 54, except that 3,4-dichloro aniline was used instead of 2,4-dichloro aniline.

¹H NMR (600 MHz, CD₃OD) δ 7.66 (s, 1H), 7.43 (d, 1H), 7.28 (d, 1H); LC-MS m/z 246.1 [M]+; mp 230~235° C.

Example 57: Preparation of N5-(2-chloro-5-trifluoromethyl)phenyl biguanide.HCl

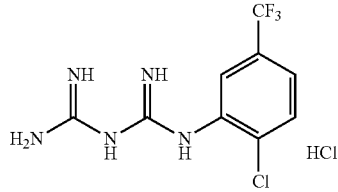 [SMILES: N=C(N)NC(=N)Nc1cc(C(F)(F)F)ccc1Cl ; Cl]

The title compound in a white solid was produced according to the substantially same method as described in Example 54, except that 2-chloro-5-trifluoromethyl aniline was used instead of 2,4-dichloro aniline.

¹H NMR (600 MHz, CD₃OD) δ 7.580 (s, 1H), 7.27 (s, 1H), 7.23 (t, 1H); LC-MS m/z 280.1 [M+1]+; mp 230~235° C.

Example 58: Preparation of N5-(3-chloro-4-fluoro)phenyl biguanide.HCl

The title compound in a white solid was produced to the substantially same method as described in Example 54, except that 3-chloro-4-fluoro aniline was used instead of 2,4-dichloro aniline.

¹H NMR (600 MHz, CD₃OD) δ 7.60 (s, 1H), 7.26 (s, 1H), 7.19 (t, 1H); LC-MS m/z 230.1 [M+1]+; mp 230~235° C.

Example 59: Preparation of N5-(2,3-dichloro)phenyl biguanide.HCl

The title compound in a white solid was produced according to the substantially same method as described in Example 54, except that 2,3-dichloro aniline was used instead of 2,4-dichloro aniline.

¹H NMR (600 MHz, CD₃OD) δ 7.58 (s, 1H), 7.34 (d, 1H), 7.28 (t, 1H); LC-MS m/z 246.0 [M]+; mp 230~235° C.

Example 60: Preparation of N5-(4-trifluoromethylthio)phenyl biguanide.HCl

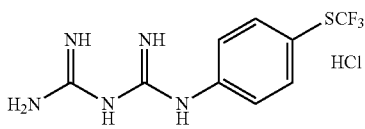

The title compound in a white solid was produced according to the substantially same method as described in Example 54, except that 4-trifluoromethylthio aniline was used instead of 2,4-dichloro aniline.

¹H NMR (600 MHz, CD₃OD) δ 7.63 (d, 2H), 7.54 (d, 2H); LC-MS m/z 278.0 [M+1]+; mp 230~235° C.

Example 61: Preparation of N1,N1-dimethyl-N5-4-(2-oxo-2-(piperidin-1-yl)ethyl thio)phenyl biguanide.HCl

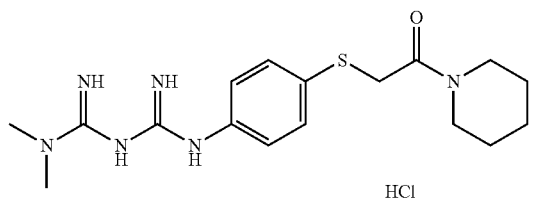 [SMILES: CN(C)C(=N)NC(=N)Nc1ccc(SCC(=O)N2CCCCC2)cc1 ; Cl]

The title compound in a white solid was produced according to the substantially same method as described in Example 54, except that 2-oxo-2-(piperidine-1-yl)ethylthio aniline was used instead of 2,4-dichloro aniline.

¹H NMR (600 MHz, CD₃OD) δ 7.40 (d, J=18 Hz, 2H), 7.32 (d, J=18 Hz, 2H), 3.76(s, 2H), 3.51(m, 4H), 3.05(s. 6H), 1.63 (m, 4H) LC-MS m/z 363.2 [M+1]

Example 62: Preparation of N1-3-pyridine-N5-(4-trifluoromethyl)phenyl biguanide.HCl

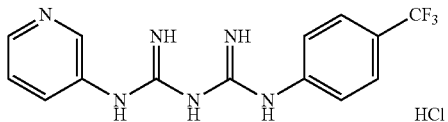 [SMILES: N=C(NC(=N)Nc1cccnc1)Nc1ccc(C(F)(F)F)cc1 ; Cl]

To a solution (20 mL) of 4-trifluoromethyl aniline (0.3 g, 1.86 mmol) dissolved in butanol was added by strong hydrochloric acid (0.16 mL, 1.86 mmol) at room temperature. The reaction mixture was added by 3-pyridine cyanoguanine (0.3 g, 1.86 mmol) prepared by Reaction Scheme 1 and then stirred with reflux for 2 hr. The reaction mixture was concentrated under reduced pressure, and then was stirred by addition of ethyl acetate 20 ml for 2 hr. The obtained solid was filtrated, was washed with ethyl acetate, and dried under reduced pressure. The title compound was produced in white solid phase (54.8 mg, 8.2%).

$^1$H NMR (600 MHz, CD$_3$OD) δ 8.50 (m, 3H), 7.79 (m, 2H), 7.65 (m, 1H), 7.60 (m, 1H), 7.53 (m, 1H) 7.47 (m, 1H); LC-MS m/z 323.2 [M+1]+; mp 251~253° C.

Example 63: Preparation of N1-3-pyridine-N5-(4-trifluoromethoxy)phenyl biguanide.HCl

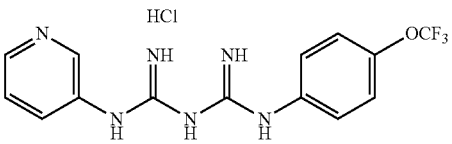 [SMILES: Cl ; N=C(NC(=N)Nc1cccnc1)Nc1ccc(OC(F)(F)F)cc1]

The title compound in a white solid was produced according to the substantially same method as described in Example 62, except that 4-trifluoromethoxy aniline was used instead of 4-trifluoromethyl aniline.

$^1$H NMR (600 MHz, CD$_3$OD) δ 8.90 (m, 1H), 8.56 (m, 1H), 8.43 (m, 1H), 8.39 (m, 1H), 7.91 (m, 1H), 7.76 (m, 2H), 7.41 (m, 1H); LC-MS m/z 339.2 [M+1]+; mp 250~252° C.

Example 64: Preparation of N1-3-pyridine-N5-(4-trifluoromethyl)benzyl biguanide.HCl

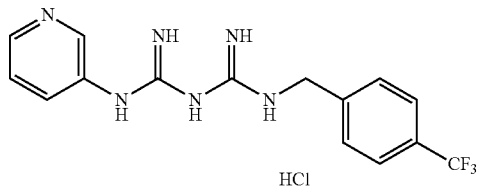 [SMILES: N=C(NCc1ccc(C(F)(F)F)cc1)NC(=N)Nc1cccnc1 ; Cl]

The title compound in a white solid was produced according to the substantially same method as described in Example 62, except that 4-trifluoromethyl benzyl amine was used instead of 4-trifluoromethyl aniline.

$^1$H NMR (600 MHz, DMSO) δ 8.49 (brs, 4H), 7.80 (m, 2H), 7.73 (m, 2H), 7.64 (m, 2H), 7.42 (m, 2H), 4.12 (s, 2H); LC-MS m/z 337.1 [M+1]+; mp 226~228° C.

Example 65: Preparation of N1-3-pyridine-N5-(4-fluoro-3-trifluoromethyl)phenyl biguanide.HCl

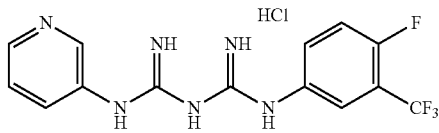 [SMILES: Cl ; N=C(NC(=N)Nc1ccc(F)c(C(F)(F)F)c1)Nc1cccnc1]

The title compound in a white solid was produced according to the substantially same method as described in Example 62, except that 4-fluoro-3-trifluoromethyl aniline was used instead of 4-trifluoromethyl aniline.

$^1$H NMR (600 MHz, CD$_3$OD) δ 8.51 (d, J=2.4 Hz, 1H), 8.29 (d, J=4.8 Hz, 1H), 7.81 (m, 1H), 7.66 (m, 1H), 7.65 (m, 1H), 7.39 (m, 1H), 7.29 (m, 1H); LC-MS m/z 341.1 [M+1]+; mp 254~256° C.

Example 66: Preparation of N1-2-pyrazine-N5-(4-trifluoromethoxy)phenyl biguanide.HCl

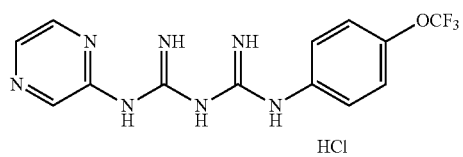 [SMILES: N=C(NC(=N)Nc1cnccn1)Nc1ccc(OC(F)(F)F)cc1 ; Cl]

The title compound in a white solid was produced according to the substantially same method as described in Example 62, except that 2-pyrazine cyanoguanidine was used instead of 3-pyridine cyanoguanine, and 4-trifluoromethoxy aniline was used instead of 4-trifluoromethyl aniline.

$^1$H NMR (600 MHz, CD$_3$OD) δ 8.53 (m, 1H), 8.28 (m, 1H), 8.02 (m, 1H), 7.92 (m, 1H), 7.55 (m, 2H), 7.42 (m, 2H); LC-MS m/z 340.0 [M+1]+; mp 223~225° C.

Example 67: Preparation of N1-2-pyrazine-N5-(4-trifluoromethyl)phenyl biguanide.HCl

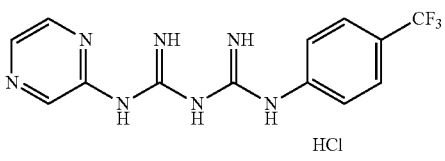 [SMILES: N=C(NC(=N)Nc1cnccn1)Nc1ccc(C(F)(F)F)cc1 ; Cl]

The title compound in a white solid was produced according to the substantially same method as described in Example 62, except that 2-pyrazine cyanoguanidine was used instead of 3-pyridine cyanoguanine, and 4-trifluoromethyl aniline was used instead of 4-trifluoromethyl aniline.

¹H NMR (600 MHz, CD₃OD) δ 8.55 (m, 1H), 8.32 (m, 1H), 7.83 (m, 1H), 7.60 (m, 2H), 7.50 (m, 2H), 7.39 (m, 1H); LC-MS m/z 324.0 [M+1]+; mp 223~225° C.

Example 68: Preparation of N1-cyclopentyl-N5-(4-trifluoromethoxy)phenyl biguanide.HCl

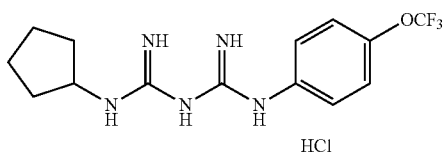 [SMILES: N=C(NC(=N)NC1CCCC1)Nc1ccc(OC(F)(F)F)cc1 ; Cl]

The title compound in a white solid was produced according to the substantially same method as described in Example 62, except that cyclopentyl cyanoguanidine was used instead of 3-pyridine cyanoguanine, and 4-trifluoromethoxy aniline was used instead of 4-trifluoromethyl aniline.

¹H NMR (600 MHz, DMSO) δ 7.60 (brs, 4H), 7.37 (m, 2H), 7.35 (m, 2H), 4.11 (m, 1H) 1.64 (m, 8H); LC-MS m/z 330.3 [M+1]+; mp 271~273° C.

Example 69: Preparation of N1-cyclopentyl-N5-(4-fluoro)phenyl biguanide.HCl

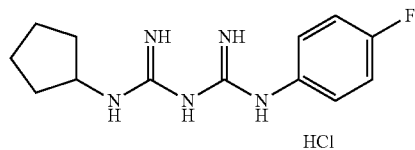 [SMILES: N=C(NC(=N)NC1CCCC1)Nc1ccc(F)cc1 ; Cl]

The title compound in a white solid was produced according to the substantially same method as described in Example 62, except that cyclopentyl cyanoguanidine was used instead of 3-pyridine cyanoguanine, and 4-fluoroaniline was used instead of 4-trifluoromethyl aniline.

¹H NMR (600 MHz, CD₃OD) δ 7.37 (m, 2H), 7.04 (m, 2H), 3.96 (brs, 1H), 2.00 (m, 2H), 1.70 (m, 2H), 1.58 (m, 4H); LC-MS m/z 264.2 [M+1]+; mp 272~274° C.

Example 70: Preparation of N1-furan-2-ylmethyl-N5-(4-chloro)phenyl biguanide.HCl

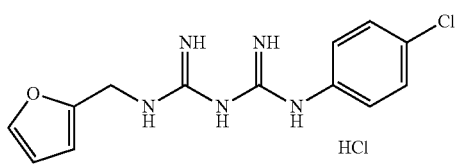 [SMILES: N=C(NCc1ccco1)NC(=N)Nc1ccc(Cl)cc1 ; Cl]

The title compound in a white solid was produced according to the substantially same method as described in Example 62, except that furan-2-ylmethyl cyanoguanidine was used instead of 3-pyridine cyanoguanine, and 4-chloro aniline was used instead of 4-trifluoromethyl aniline.

¹H NMR (600 MHz, CD₃OD) δ 7.43 (m, 1H), 7.29 (m, 4H), 6.34 (m, 1H), 6.22 (m, 1H), 4.37 (s, 2H); LC-MS m/z 292.2 [M+1]+; mp 221~223° C.

Example 71: Preparation of N1-furan-2-ylmethyl-N5-(4-trifluoromethoxy)phenyl biguanide.HCl

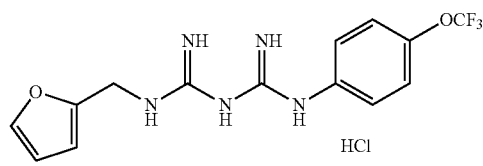 [SMILES: N=C(NCc1ccco1)NC(=N)Nc1ccc(OC(F)(F)F)cc1 ; Cl]

The title compound in a white solid was produced according to the substantially same method as described in Example 62, except that furan-2-ylmethyl cyanoguanidine was used instead of 3-pyridine cyanoguanine, and 4-trifluoromethoxy aniline was used instead of 4-trifluoromethyl aniline.

¹H NMR (600 MHz, CD₃OD) δ 7.42 (m, 3H), 7.18 (m, 2H), 6.33 (m, 2H), 4.38 (s, 2H); LC-MS m/z 342.1 [M+1]+; mp 223~225° C.

Example 72: Preparation of N1-furan-2-ylmethyl-N5-(4-trifluoromethyl)phenyl biguanide.HCl

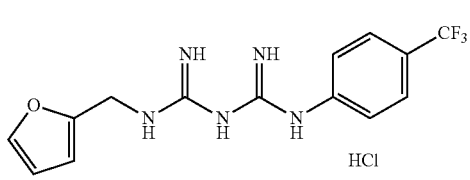 [SMILES: N=C(NCc1ccco1)NC(=N)Nc1ccc(C(F)(F)F)cc1 ; Cl]

The title compound in a white solid was produced according to the substantially same method as described in Example 62, except that furan-2-ylmethyl cyanoguanidine was used instead of 3-pyridine cyanoguanine, and 4-trifluoromethyl aniline was used instead of 4-trifluoromethyl aniline.

¹H NMR (600 MHz, CD₃OD) δ 7.51 (m, 3H), 7.41 (m, 1H), 6.33 (m, 2H), 4.38 (s, 2H); LC-MS m/z 326.2 [M+1]+; mp 231~233° C.

Example 73: Preparation of N1-dihydropyridine-N5-(4-(2-aminoethyl)phenyl biguanide.HCl

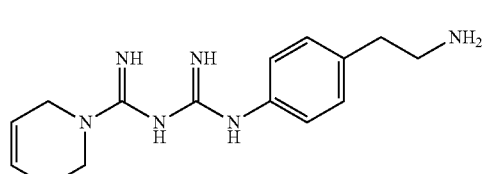

The title compound in a white solid was produced according to the substantially same method as described in Example 62, except that dihydropyridine cyanoguanidine was used instead of 3-pyridine cyanoguanine, and 4-(2-aminoethyl)aniline was used instead of 4-trifluoromethyl aniline.

¹H NMR (600 MHz, CD₃OD) δ 7.37 (d, 2H), 7.26 (d, 2H), 5.95 (m, 1H), 5.73 (m, 1H), 3.99 (s, 2H), 3.64 (t, 2H), 3.16 (t, 2H), 2.94 (t, 2H), 2.23 (s, 2H); LC-MS m/z 287.2 [M+1]; mp 230~235° C.

Example 74: Preparation of N1-phenyl-N5-(3-trifluoromethyl)benzyl biguanide.HCl

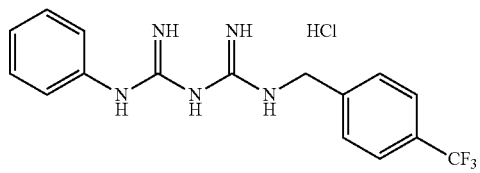 [SMILES: N=C(NCc1ccc(C(F)(F)F)cc1)NC(=N)Nc1ccccc1 ; Cl]

The title compound in a white solid was produced according to the substantially same method as described in Example 62, except that phenyl cyanoguanidine was used instead of 3-pyridine cyanoguanine, and 3-trifluoromethylbenzyl amine was used instead of 4-trifluoromethyl aniline.

¹H NMR (400 MHz, CD₃OD) δ 761 (d, J=7.8 Hz, 2H), 7.46 (d, J=7.8 Hz, 2H), 7.25 (m, 4H), 7.13 (m, 1H), 4.55 (s, 2H) LC-MS m/z 336.1 [M+1]

Example 75: Preparation of N1-(4-trifluoromethoxy)phenyl-N5-(N-biphenyl-4-yl) biguanide.HCl

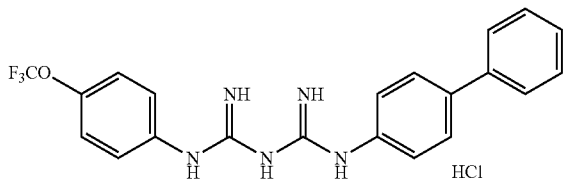 [SMILES: N=C(NC(=N)Nc1ccc(-c2ccccc2)cc1)Nc1ccc(OC(F)(F)F)cc1 ; Cl]

The title compound in a white solid was produced according to the substantially same method as described in Example 62, except that 4-trifluoromethoxy phenyl cyanoguanidine was used instead of 3-pyridine cyanoguanine, and 3-trifluoromethylbenzyl amine 4-biphenyl amine was used instead of 4-trifluoromethyl aniline.

¹H NMR (600 MHz, CD₃OD) δ 7.41 (m, 4H), 7.41 (m, 4H), 7.33 (m, 12H), 7.32 (m, 2H), 7.26 (m, 2H) LC-MS m/z 415.2 [M+1]

Example 76: Preparation of N1-3-phenoxyphenyl-N5-(4-trifluoromethoxy)phenyl biguanide.HCl

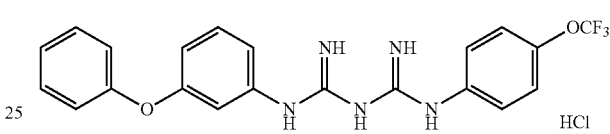

The title compound in a white solid was produced according to the substantially same method as described in Example 62, except that 3-phenoxy phenyl cyanoguanidine was used instead of 3-pyridine cyanoguanine, and 3-trifluoromethylbenzyl amine 4-trifluoromethoxy aniline was used instead of 4-trifluoromethyl aniline.

¹H NMR (600 MHz, CD₃OD) δ 7.47 (m, 2H), 7.21 (m, 2H), 4.15 (m, 1H), 3.34 (m, 2H), 2.07 (m, 3H), 1.71 (m, 1H), 1.18 (s, 3H) LC-MS m/z 466.2 [M+1]

Example 77: Preparation of N-(4-(3-(imino(pyrrolidin-1-yl)methyl)guanidino)phenethyl)-5-(2-oxohexahydro-1H-thieno[2,3-d]imidazol-5-yl)pentaneamide

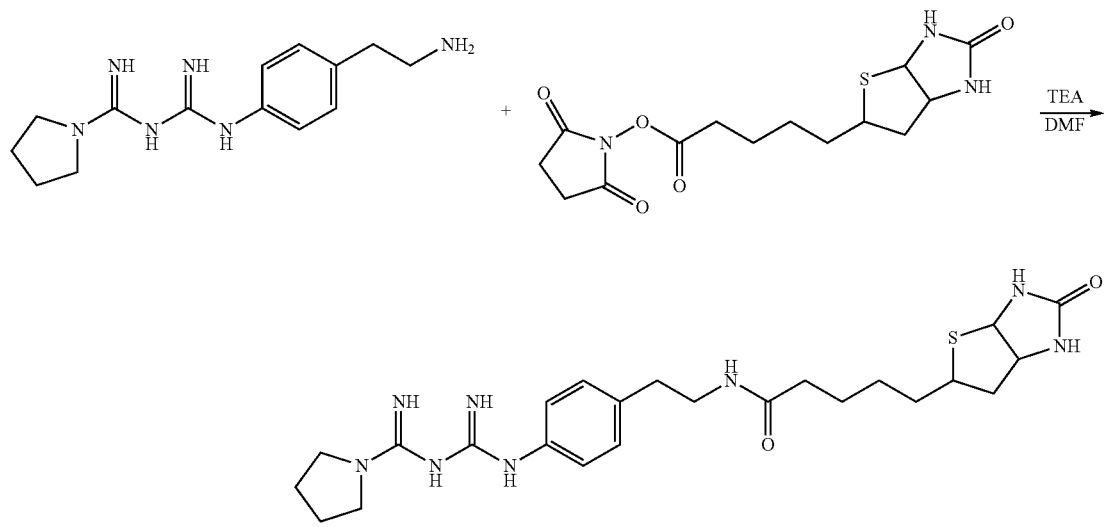

N—(N-(4-(2-aminoethyl)phenyl)carbamimidoyl)pyrrolidine-1-carboximidamide (0.12 g, 0.48 mmol) and 2,5-dioxopyrrolidin-1-yl-5-(2-oxohexahydro-1H-thieno[2,3-d]imidazol-5-yl)pentanoate (0.20 g, 0.59 mmol) were dissolved in anhydrous DMF (5 ml), and then triethylamine (0.2 ml, 1.47 mmol) was added thereto. After stirring the reaction mixture for 24 hr, the reaction mixture was distilled under reduced pressure, separated and purified by a chromatography using MC:MeOH=10:1. The title compound was produced in white solid phase (84.0 mg, 34.2%).

$^1$H NMR (600 MHz, CD$_3$OD) δ 7.33 (d, 2H), 7.18 (d, 2H), 4.51 (m, 1H), 4.30 (m, 1H), 3.48 (m, 4H), 3.41 (m, 2H), 3.18 (m, 1H), 2.94 (dd, 1H), 2.77 (t, 2H), 2.72 (d, 1H), 2.17 (t, 2H), 2.04, 1.59 (d, 4H), 1.71~1.38 (m, 6H); LC-MS m/z 501.3 [M+1]; mp 230~235° C.

Example 78: Preparation of N-(4-(3-(imino(2-methylpiperidin-1-yl)methyl)guanidino)phenethyl)-5-(2-oxohexahydro-1H-thieno[2,3-d]imidazol-5-yl)pentanamide

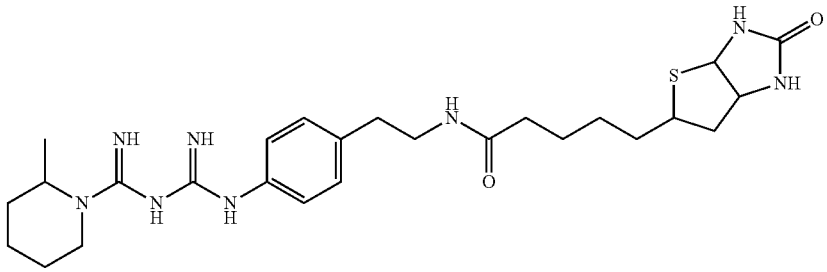 [SMILES: CC1CCCCN1C(=N)NC(=N)Nc1ccc(CCNC(=O)CCCCC2CC3NC(=O)NC3S2)cc1]

The title compound was produced according to the substantially same method as described in Example 92, except that N—(N-(4-(2-aminoethyl)phenyl)carbamimidoyl)-2-methylpiperidine-1-carboximidamide was used instead of 4-N—(N-(4-(2-aminoethyl)phenyl)carbamimidoyl)pyrrolidine-1-carboximidamide.

$^1$H NMR (600 MHz, CD$_3$OD) δ 7.29 (d, 2H), 7.19 (d, 2H), 4.51 (m, 1H), 4.40 (s, 1H), 4.30 (m, 1H), 3.95 (d, 1H), 3.41 (m, 2H), 3.19 (m, 1H), 3.09 (t, 1H), 2.94 (dd, 1H), 2.77 (t, 2H), 2.72 (d, 1H), 2.17 (t, 2H), 1.74~1.35 (m, 12H), 1.24 (d, 3H); LC-MS m/z 529.3 [M+1]; mp 230~235° C.

Example 79: Preparation of N-(4-(3-((3,5-dimethylpiperidin-1-yl)(imino)methyl)guanidino)phenethyl)-5-(2-oxohexahydro-1H-thieno[2,3-d]imidazol-5-yl)pentanamide

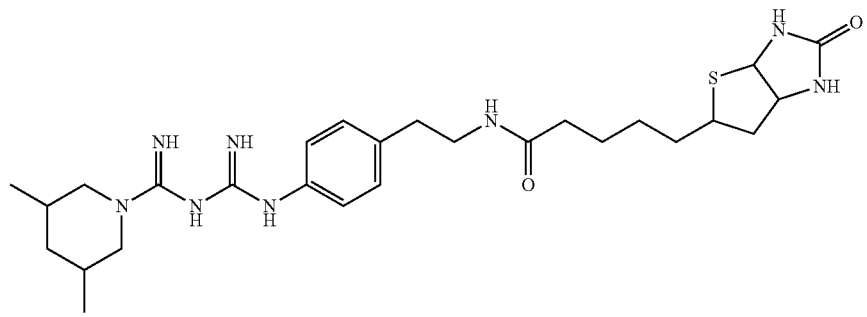 [SMILES: CC1CC(C)CN(C(=N)NC(=N)Nc2ccc(CCNC(=O)CCCCC3CC4NC(=O)NC4S3)cc2)C1]

The title compound was produced according to the substantially same method as described in Example 92, except that N—(N-(4-(2-aminoethyl)phenyl)carbamimidoyl)-3,5-dimethylpiperidine-1-carboximidamide was used instead of 4-N—(N-(4-(2-aminoethyl)phenyl)carbamimidoyl)pyrrolidine-1-carboximidamide.

$^1$H NMR (600 MHz, CD$_3$OD) δ 7.31 (d, 2H), 7.19 (d, 2H), 4.51 (m, 1H), 4.30 (m, 1H), 4.05 (s, 2H), 3.41 (m, 2H), 3.19 (m, 1H), 2.94 (dd, 1H), 2.77 (t, 2H), 2.72 (d, 1H), 2.45 (t, 2H), 2.17 (t, 2H), 1.86 (d, 1H), 1.73~1.55 (m, 6H), 1.38 (m, 2H), 0.92 (d, 6H), 0.84 (m, 1H); LC-MS m/z 543.4 [M+1]; mp 230~235° C.

Example 80: Preparation of N-(4-(3-((5,6-dihydropyridin-1(2H)-yl)(imino)methyl)guanidino)phenethyl)-5-(2-oxohexahydro-1H-thieno[2,3-d]imidazol-5-yl)pentanamide

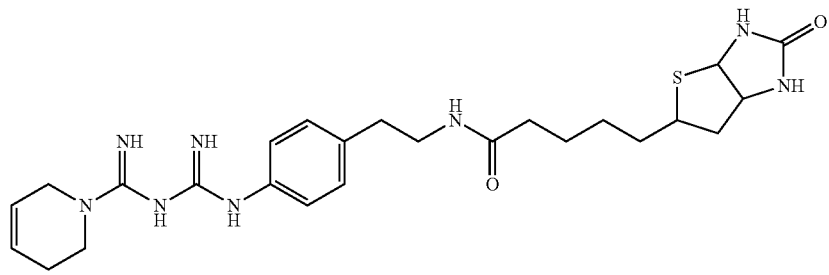 [SMILES: N=C(NC(=N)N1CC=CCC1)Nc1ccc(CCNC(=O)CCCCC2CC3NC(=O)NC3S2)cc1]

The title compound was produced according to the substantially same method as described in Example 92, except that N—(N-(4-(2-aminoethyl)phenyl)carbamimidoyl)-5,6-dihydropyridine-1(2H)-carboximidamide was used instead of 4-N—(N-(4-(2-aminoethyl)phenyl)carbamimidoyl)pyrrolidine-1-carboximidamide.

$^1$H NMR (600 MHz, CD$_3$OD) δ 7.28 (d, 2H), 7.20 (d, 2H), 5.95 (m, 1H), 5.74 (m, 1H), 4.50 (m, 1H), 4.29 (m, 1H), 3.98 (s, 2H), 3.62 (t, 2H), 3.40 (m, 2H), 3.19 (m, 1H), 2.94 (dd, 1H), 2.77 (t, 2H), 2.72 (d, 1H), 2.23 (s, 2H), 2.16 (t, 2H), 1.71~1.37 (m, 6H); LC-MS m/z 513.3 [M+1]; mp 230~235° C.

Example 81: Preparation of N-(4-(3-(((2R,6S)-2,6-dimethylpiperidin-1-yl)(imino)methyl)guanidino)phenethyl)-5-(2-oxohexahydro-1H-thieno[2,3-d]imidazol-5-yl)pentanamide

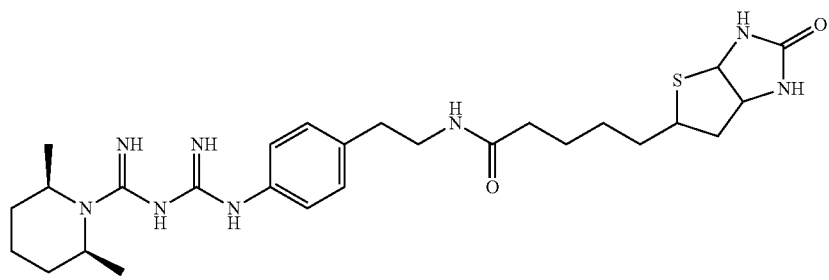 [SMILES: C[C@@H]1CCC[C@H](C)N1C(=N)NC(=N)Nc1ccc(CCNC(=O)CCCCC2CC3NC(=O)NC3S2)cc1]

The title compound was produced according to the substantially same method as described in Example 92, except that (2R,6S)—N—(N-(4-(2-aminoethyl)phenyl)carbamimidoyl)-2,6-dimethylpiperidine-1-carboximidamide was used instead of 4-N—(N-(4-(2-aminoethyl)phenyl)carbamimidoyl)pyrrolidine-1-carboximidamide.

$^1$H NMR (600 MHz, CD$_3$OD) δ 7.27 (m, 2H), 7.14 (m, 2H), 4.47 (m, 1H), 4.26 (m, 1H), 3.37 (m, 2H), 3.18 (m, 2H), 2.91 (m, 1H) 2.75 (m, 3H), 2.15 (m, 2H), 1.67 (m, 13H) 1.26 (m, 6H); LC-MS m/z 543.2 [M+1]+

Example 82: Preparation of N-(4-(3-(imino(pyrrolidin-1-yl)methyl)guanidino)phenyl)-5-(2-oxohexahydro-1H-thieno[2,3-d]imidazol-5-yl)pentanamide

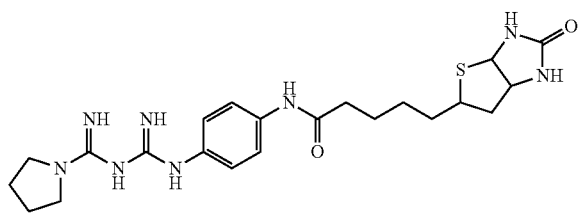 [SMILES: N=C(NC(=N)N1CCCC1)Nc1ccc(NC(=O)CCCCC2CC3NC(=O)NC3S2)cc1]

The title compound was produced according to the substantially same method as described in Example 92, except that N—(N-(4-aminophenyl)carbamimidoyl)pyrrolidine-1-carboximidamide was used instead of 4-N—(N-(4-(2-aminoethyl)phenyl)carbamimidoyl)pyrrolidine-1-carboximidamide.

$^1$H NMR (600 MHz, CD$_3$OD) δ 7.53 (d, 2H), 7.31 (d, 2H), 4.49 (m, 1H), 4.31 (m, 1H), 3.48 (s, 4H), 3.22 (m, 1H), 2.93 (dd, 1H), 2.71 (d, 1H), 2.03 (d, 4H), 1.80~1.47 (m, 6H); LC-MS m/z 473.3 [M+1]; mp 230~235° C.

Example 83: Preparation of 2-(6-hydroxy-3-oxo-3H-xanthen-9-yl)-N-(4-(3-(imino(pyrrolidin-1-yl)methyl)guanidino)benzyl)benzamide

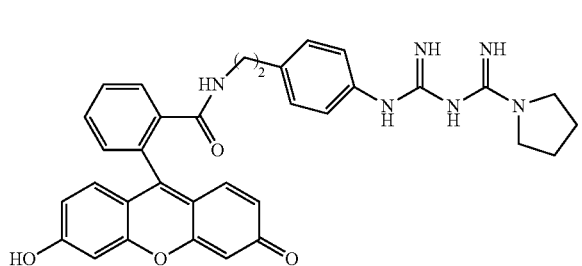

The title compound was produced according to the substantially same method as described in Example 92, except that 2,5-dioxopyrrolidin-1-yl 2-(6-hydroxy-3-oxo-3H-xanthen-9-yl)benzoate was used instead of 2,5-dioxopyrrolidin-1-yl-5-(2-oxohexahydro-1H-thieno[2,3-d]imidazol-5-yl)pentanoate.

$^1$H NMR (600 MHz, CD$_3$OD) δ 7.90 (d, 1H), 7.57 (m, 2H), 7.17 (d, 2H), 7.09 (d, 1H), 6.88 (d, 2H), 6.66 (d, 2H), 6.46 (dd, 2H), 6.38 (d, 2H), 3.45 (d, 4H), 3.18 (t, 2H), 2.35 (t, 2H), 2.01 (d, 4H); LC-MS m/z 589.2 [M+1]+; mp 230~235° C.

Example 84: Preparation of N-(4-(3-(((2R,6S)-2,6-dimethylpiperidin-1-yl)(imino)methyl)guanidino)benzyl)-2-(6-hydroxy-3-oxo-3H-xanthen-9-yl)benzamide

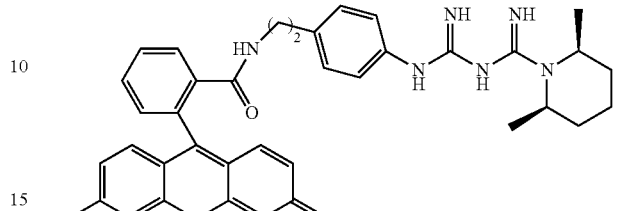

The title compound was produced according to the substantially same method as described in Example 92, except that N—(N-(4-(2-aminoethyl)phenyl)carbamimidoyl)-2,6-dimethylpiperidine-1-carboximidamide was used instead of N—(N-(4-(2-aminoethyl)phenyl)carbamimidoyl)pyrrolidine-1-carboximidamide, and 2,5-dioxopyrrolidin-1-yl 2-(6-hydroxy-3-oxo-3H-xanthen-9-yl)benzoate was used instead of 2,5-dioxopyrrolidin-1-yl-5-(2-oxohexahydro-1H-thieno[2,3-d]imidazol-5-yl)pentanoate.

$^1$H NMR (600 MHz, CD$_3$OD) δ 7.38 (d, 2H), 7.25 (d, 2H), 4.60~4.40 (s, 2H), 3.16 (t, 2H), 2.94 (t, 2H), 1.90~1.51 (m, 6H) 1.30 (s, 6H); LC-MS m/z 317.3 [M+1]; mp 230~235° C.

Example 85: Preparation of N-(4-(3-((3,5-dimethylpiperidin-1-yl)(imino)methyl)guanidino)benzyl)-2-(6-hydroxy-3-oxo-3H-xanthen-9-yl)benzamide

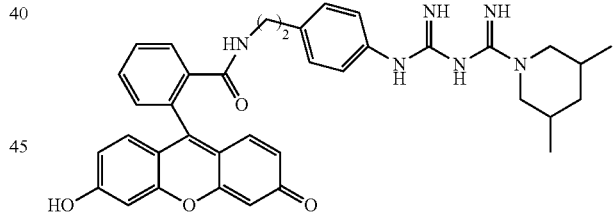

The title compound was produced according to the substantially same method as described in Example 92, except that N—(N-(4-(2-aminoethyl)phenyl)carbamimidoyl)-3,5-dimethylpiperidine-1-carboximidamide was used instead of N—(N-(4-(2-aminoethyl)phenyl)carbamimidoyl)pyrrolidine-1-carboximidamide, and 2,5-dioxopyrrolidin-1-yl 2-(6-hydroxy-3-oxo-3H-xanthen-9-yl)benzoate was used instead of 2,5-dioxopyrrolidin-1-yl-5-(2-oxohexahydro-1H-thieno[2,3-d]imidazol-5-yl)pentanoate.

$^1$H NMR (600 MHz, CD$_3$OD) δ 7.90 (d, 1H), 7.58 (m, 2H), 7.14 (d, 2H), 7.10 (d, 1H), 6.90 (d, 2H), 6.66 (d, 2H), 6.46 (dd, 2H), 6.39 (d, 2H), 3.98 (s, 2H), 3.18 (t, 2H), 2.41 (m, 2H), 2.36 (t, 2H), 1.83 (d, 1H), 1.60 (m, 2H), 0.89 (d, 6H), 0.81 (m, 1H); LC-MS m/z 631.4 [M+1]+; mp 230~235° C.

Example 86: Preparation of 2-(6-hydroxy-3-oxo-3H-xanthene-9-yl)-N-(4-(3-(imino(3-methylpiperidine-1-yl)methyl)guanidino)benzyl)benzamide

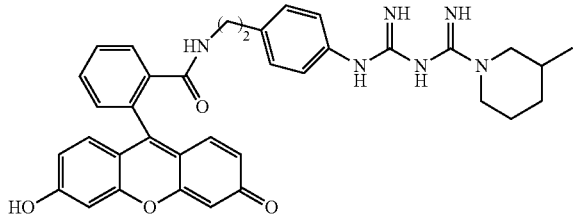

The title compound was produced according to the substantially same method as described in Example 92, except that N—(N-(4-(2-aminoethyl)phenyl)carbamimidoyl)-3-methylpiperidine-1-carboximidamide was used instead of N—(N-(4-(2-aminoethyl)phenyl)carbamimidoyl)pyrrolidine-1-carboximidamide, and 2,5-dioxopyrrolidin-1-yl 2-(6-hydroxy-3-oxo-3H-xanthen-9-yl)benzoate was used instead of 2,5-dioxopyrrolidin-1-yl-5-(2-oxohexahydro-1H-thieno[2,3-d]imidazol-5-yl)pentanoate.

Example 87: Preparation of N—(N-(4-(trifluoromethoxy)phenyl)carbamimidoyl)-3,4-dihydroisoquinolin-2(1H)-carboximidamide.HCl

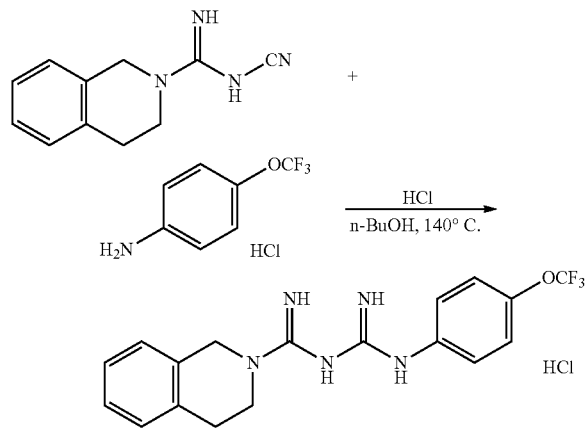

The title compound was produced according to the substantially same method as described in Example 1, except that dihydro isoquinolin cyanoguanidine was used instead of pyrrolidine cyanoguanidine, and 4-(trifluoromethoxy)aniline was used instead of piperonyl amine.

$^1$H NMR (400 MHz, DMSO-d6) δ 9.87 (s, 1H), 7.84 (s, 2H), 7.51 (d, J=7.2 Hz, 2H), 7.29 (d, J=7.6 Hz, 2H), 7.22 (s, 4H), 7.00 (s, 2H), 4.63 (s, 2H), 3.65 (s, 2H), 2.89 (s, 2H); LC-MS m/z 378.2 [M+1]

Example 88: Preparation of N—(N-(4-(trifluoromethoxy)phenyl)carbamimidoyl)indoline-1-carboximidamide.HCl

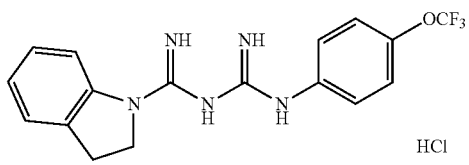 [SMILES: N=C(NC(=N)N1CCc2ccccc21)Nc1ccc(OC(F)(F)F)cc1 ; Cl]

The title compound was produced according to the substantially same method as described in Example 1, except that indoline cyanoguanidine was used instead of pyrrolidine cyanoguanidine, and 4-(trifluoromethoxy)aniline was used instead of piperonyl amine.

$^1$H NMR (600 MHz, CD$_3$OD) δ 7.69 (d, J=8.4 Hz, 1H), 7.48 (m, 2H), 7.25 (m, 3H), 7.10 (m, 1H), 7.03 (m, 1H), 4.05 (m, 2H), 3.24 (m, 2H); LC-MS m/z 364.2 [M+1]

Example 89: Preparation of N-(imino(pyrrolidin-1-yl)methyl)-3,4-dihydroisoquinoline-2(1H)-carboximidamide HCl

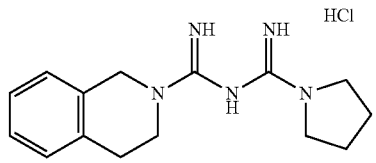 [SMILES: Cl ; N=C(NC(=N)N1CCc2ccccc2C1)N1CCCC1]

The title compound was produced according to the substantially same method as described in Example 1, except that dihydroisoquinolin-2(1H) cyanoguanidine was used instead of pyrrolidine cyanoguanidine, and pyrrolidine was used instead of piperonyl amine.

$^1$H NMR (600 MHz, CD$_3$OD) δ 7.21 (m, 3H), 7.18 (m, 1H), 4.68, (s, 2H), 3.74 (t, J=6.6 Hz, 2H), 3.46 (s, 4H), 2.95 (t, J=6.0 Hz, 2H), 2.00 (s, 4H); LC-MS m/z 272.2 [M+1]

Example 90: Preparation of N—(N-(4-phenoxyphenyl)carbamimidoyl)indoline-1-carboximidamide HCl

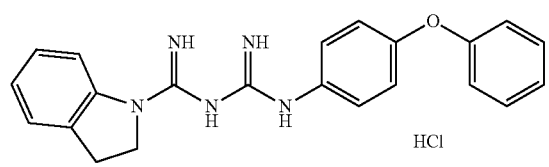 [SMILES: N=C(NC(=N)N1CCc2ccccc21)Nc1ccc(Oc2ccccc2)cc1 ; Cl]

The title compound was produced according to the substantially same method as described in Example 1, except that indoline cyanoguanidine was used instead of pyrrolidine cyanoguanidine, and 4-phenoxy aniline was used instead of piperonyl amine.

$^1$H NMR (600 MHz, CD$_3$OD) δ 7.73 (d, J=7.8 Hz, 1H), 7.32 (m, 4H), 7.23 (m, 1H), 7.10 (m, 2H), 7.02 (t, J=7.2 Hz, 1H), 6.97 (m, 4H), 4.03 (t, J=8.4 Hz, 2H), 3.22 (t, J=8.4 Hz, 2H); LC-MS m/z 372.2 [M+1]

Example 91: Preparation of N—(N-(3-phenoxyphenyl)carbamimidoyl)indoline-1-carboximidamide HCl

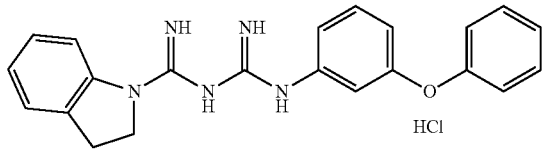 [SMILES: N=C(NC(=N)N1CCc2ccccc21)Nc1cccc(Oc2ccccc2)c1 ; Cl]

The title compound was produced according to the substantially same method as described in Example 1, except that indoline cyanoguanidine was used instead of pyrrolidine cyanoguanidine, and 3-phenoxy aniline was used instead of piperonyl amine $^1$H NMR (600 MHz, CD$_3$OD) δ 7.67 (m, 1H), 7.28 (m, 2H), 7.21 (m, 2H), 7.10 (m, 5H), 6.92 (m, 2H), 6.78 (m, 41H), 4.00 (m, 2H), 3.24 (m, 2H); LC-MS m/z 372.2 [M+1]

Example 92: Preparation of N-(5-(trifluoromethoxy)-1H-benzo[d]imidazol-2-yl)pyrrolidine-1-carboximidamide HCl

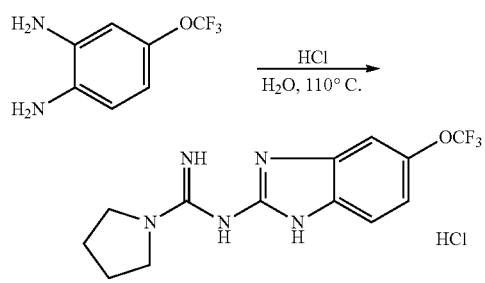

N1-pyrrolidine cyanoguanidine (72 mg, 0.52 mmol) and 4-trifluoro methoxy phenylene diamine (0.1 g, 0.52 mmol) were dissolved in distilled water (10 ml) at room temperature, and then hydrochloric acid (0.1 ml, 1.04 mmol) was added thereto, and stirred with reflux at 110° C. for 2 hr. The reaction mixture was added by 10% potassium hydroxide solution, and then the obtained solid was filtrated under reduced pressure, and was washed with distilled water. The filtrated solid was dried under reduced pressure. The title compound was produced in brown solid phase (20 mg, 12.2%).

$^1$H NMR (600 MHz, CD$_3$OD) δ 7.22 (d, J=8.4 Hz, 1H), 7.13 (s, 1H), 6.90 (d, J=8.4 Hz, 1H), 3.49 (br s, 4H), 1.92 (s, 4H); LC-MS m/z 235.1 [M+1]

Example 93: Preparation of N-(5-fluoro-1H-benzo[d]imidazol-2-yl)pyrrolidine-1-carboximidamide HCl

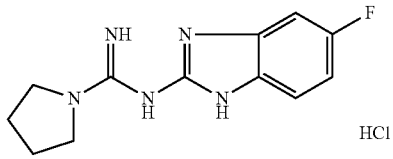 [SMILES: N=C(Nc1nc2cc(F)ccc2[nH]1)N1CCCC1 ; Cl]

The title compound was produced according to the substantially same method as described in Example 92, except that 4-fluoro phenylene diamine was used instead of 4-trifluoro methoxy phenylene diamine $^1$H NMR (600 MHz, CD$_3$OD) δ 7.15 (d, J=8.4 Hz, 1H), 6.95 (d, J=9.0 Hz, 1H), 6.72 (t, J=10.2 Hz, 1H), 3.48 (s, 4H), 1.98 (s, 4H); LC-MS m/z 248.0 [M+1]

Example 94: Preparation of N-(5-methyl-1H-benzo[d]imidazol-2-yl)pyrrolidine-1-carboximidamide HCl

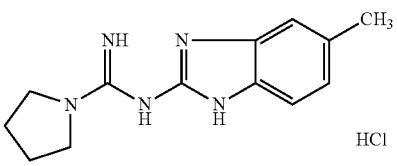 [SMILES: Cc1ccc2[nH]c(NC(=N)N3CCCC3)nc2c1 ; Cl]

The title compound was produced according to the substantially same method as described in Example 92, except that 4-methyl phenylene diamine was used instead of 4-trifluoro methoxy phenylene diamine.

$^1$H NMR (600 MHz, CD$_3$OD) 7.13 (d, J=7.8 Hz, 1H), 7.06 (s, 1H), 6.84 (d, J=7.2 Hz, 1H), 3.47 (s, 4H), 2.37 (s, 3H), 1.96 (s, 4H); LC-MS m/z 244.0 [M+1]

Example 95: Preparation of N-(5-methoxy-1H-benzo[d]imidazol-2-yl)pyrrolidine-1-carboximidamide.HCl

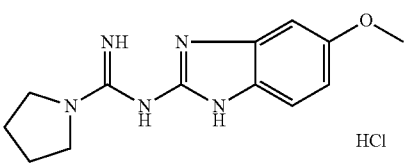 [SMILES: COc1ccc2[nH]c(NC(=N)N3CCCC3)nc2c1 ; Cl]

The title compound was produced according to the substantially same method as described in Example 92, except that 4-methoxy phenylene diamine was used instead of 4-trifluoro methoxy phenylene diamine.

$^1$H NMR (600 MHz, CD$_3$OD) 7.13 (d, J=7.8 Hz, 1H), 6.85 (d, J=2.4 Hz, 1H), 6.65 (dd, J=9.0 Hz, J=2.4 Hz, 1H), 3.78 (s, 3H), 3.48 (s, 4H), 1.98 (s, 4H); LC-MS m/z 260.1 [M+1]

Example 96: Preparation of N-(1H-benzo[d]imidazol-2-yl)pyrrolidine-1-carboximidamide HCl

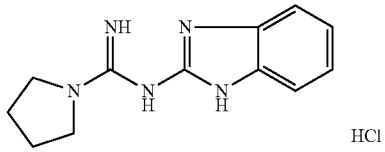 [SMILES: N=C(Nc1nc2ccccc2[nH]1)N1CCCC1 ; Cl]

The title compound was produced according to the substantially same method as described in Example 92, except that o-phenylene diamine was used instead of 4-trifluoro methoxy phenylene diamine.

$^1$H NMR (600 MHz, CD$_3$OD) 7.25 (d, J=8.4 Hz, 2H), 7.00 (d, J=9.0 Hz, 2H), 3.48 (s, 4H), 1.98 (s, 4H); LC-MS m/z 230.1 [M+1]

Experimental Example

The compounds produced in Examples 1 to 96 were evaluated for their inhibitory activities on cancer cells according to the following method.

Experimental Example 1: Evaluation of Inhibitory Activity against Cancer Cells The inhibitory activities of biguanide derivatives against cancer cells were evaluated in the cell line SK-MEL-28 derived from human Melanoma cell, Miapaka-2 cell line derived from human pancreatic cancer cell and HCT116 cell line derived from human colorectal cancer cell by measuring the concentration that inhibits 50% of the growth of the cell lines (the half maximal inhibitory concentration, IC$_{50}$).

Firstly, SK-MEL-28 cells were grown to be density of 5,000 cells/well in RPMI-1640 media supplemented with 10% (v/v) bovine calf serum, on 96-well plates for 16 hr. To measure the IC$_{50}$ of each compound, the cells were incubated for 48 hr with the 100 mM PBS stock compounds at an amount of 10 mM, 1 mM, 200 uM, 40 uM, 8 uM, 1.6 uM, 0.32 uM or 0.064 uM; 50 mM PBS and EtOH stock compounds at an amount of 1 mM, 200 uM, 40 uM, 8 uM, 1.6 uM, 0.32 uM and 0.064 uM; and 50 mM DMSO stock compounds at an amount of 100 uM, 25 uM, 6.25 uM, 1.56 uM, 0.39 uM, 0.10 uM and 0.02 uM, respectively. To test the viable cells after incubation with each compound, the cell cultures were incubated additionally for 2 hr in the presence of MTT. The produced formazan crystals were dissolved with dimethyl sulfoxide and then measured by detecting the absorbance at 560 nm.

After the 48 hr incubation, the viable cells were counted on the well plates treated with the compounds of the Examples relative to the count of the viable cells on the non-treated plates, and then was represented as the cell viability (%). By using the cell viability (%) result, the cell viability curve was plotted, and IC$_{50}$ was calculated from the curve to evaluate the inhibitory activity against cancer cells.

The inhibitory activities of biguanide derivatives against cancer cells of Miapaca-2 cell and HCT116 cell were evaluated according to the substantially same method as described in SK-MEL-28 cell, except that DMEM media supplemented with 10% (v/v) bovine calf serum was used instead of RPMI-1640 media supplemented with 10% (v/v) bovine calf serum for SK-MEL-28 cell.

The experimental results of inhibitory activity against cancer cells are summarized in Table 1 as below.

Experimental Example 2: Evaluation of Inhibitory Activity on Oxygen Consumption Rate (OCR)

The cellular metabolic activity of the compounds on Oxygen Consumption Rate (OCR) was evaluated, because the biguanide drugs have anticancer activity by inhibiting the oxidative phosphorylation of cancer cell.

Compared to phenformin, the more effective compounds were selected by evaluating the inhibitory activity on the cell OCR, after lung cancer cell line A549 (ATCC-American Type Culture Collection) was treated with the compounds of Examples.

A549 cells were inoculated at 5×10$^3$ cells in RPMI1640 media on XF96 cell culture plate and cultured for 24 h (temp; 37° C., 5% CO$_2$) to make the cell adhere to the plate.

After 24 hr, A549 cells were treated by 10 μM of the compounds or phenformin, and were washed with XF analysis media using Prep station to remove the original media. A549 cells were retreated by compounds or phenformin and incubated for 1 hr (temp; 37° C., Non-CO$_2$) in Prep station. While incubation in Prep station, sensor cartridge was calibrated for 1 hr. Then, the calibrated sensor cartridge was inserted to the cell plate to analyze OCR.

When OCR of phenformin as a reference drug was set to 100% and OCR of untreated control was set to 0%, the OCR of tested compounds was calculated by converting the measured OCR to be the relative percentage value (%). The results are summarized in Table 1, below.

TABLE 1

| Test Compound | Inhibitory activity against cancer cells | | | OCR % to phenformin |
|---|---|---|---|---|
| | SK-MEL-28 IC$_{50}$ (μM) | Miapaca-2 IC$_{50}$ (μM) | HCT 116 IC$_{50}$ (μM) | (A549, 3 hrs) 10 uM |
| Phenformin | 265.8878 | 118.52 | 12.5 | — |
| Example 1 | 106.99 | 36.22 | >100 | — |
| Example 2 | — | — | >100 | — |
| Example 3 | — | — | >100 | — |
| Example 4 | — | — | >100 | — |
| Example 5 | — | — | >100 | — |
| Example 6 | — | — | 28.6 | 44% |
| Example 8 | — | — | 6.97 | — |
| Example 9 | — | — | 7.427 | — |
| Example 10 | — | — | 6.281 | — |
| Example 11 | — | — | 6.464 | — |
| Example 12 | — | — | 81.9 | — |
| Example 13 | — | — | >100 | — |
| Example 14 | 29.4732 | 26.63 | >100 | — |
| Example 15 | — | — | 711.8 | — |
| Example 16 | — | — | 39.810 | 13% |
| Example 17 | 183.82 | 113.14 | >100 | — |
| Example 18 | 181.71 | 47.92 | >100 | 57% |
| Example 19 | — | — | >100 | — |
| Example 20 | 134.15 | 58.62 | >100 | 15% |
| Example 21 | — | — | >100 | — |
| Example 22 | — | 105.7 | — | 74% |
| Example 23 | >1000 | 2339.56 | >100 | — |
| Example 24 | >100 | >100 | >100 | — |
| Example 25 | — | — | >100 | — |
| Example 26 | — | — | >100 | — |
| Example 27 | — | — | >100 | — |
| Example 28 | 176.3578 | 208.85 | >100 | — |
| Example 29 | — | — | >100 | — |
| Example 30 | — | — | >100 | — |
| Example 31 | — | — | 93.6 | — |
| Example 32 | — | — | 90.3 | — |
| Example 33 | — | — | >100 | — |
| Example 34 | — | — | >100 | — |

TABLE 1-continued

| Test Compound | Inhibitory activity against cancer cells | | | OCR % to phenformin (A549, 3 hrs) 10 uM |
|---|---|---|---|---|
| | SK-MEL-28 IC$_{50}$ (μM) | Miapaca-2 IC$_{50}$ (μM) | HCT 116 IC$_{50}$ (μM) | |
| Example 35 | — | — | 32.4 | — |
| Example 36 | — | — | 7.1 | — |
| Example 37 | — | — | 32.3 | — |
| Example 38 | — | — | 11.7 | — |
| Example 39 | — | — | 7.5 | — |
| Example 40 | — | — | 35.2 | 42.9% |
| Example 41 | — | — | >100 | — |
| Example 42 | — | — | >100 | — |
| Example 43 | — | — | >100 | — |
| Example 44 | — | — | 42.2 | — |
| Example 45 | — | — | 33.8 | — |
| Example 46 | — | — | >100 | — |
| Example 47 | — | — | >100 | — |
| Example 48 | — | — | >100 | — |
| Example 49 | — | — | >100 | — |
| Example 50 | — | — | >100 | — |
| Example 51 | — | — | 7.828 | — |
| Example 52 | — | — | 7.654 | — |
| Example 53 | >100 | >100 | 182.1 | — |
| Example 54 | — | — | >100 | — |
| Example 55 | — | — | >100 | — |
| Example 56 | — | — | 34.8 | — |
| Example 57 | — | — | >100 | — |
| Example 58 | — | — | >100 | — |
| Example 59 | — | — | >100 | — |
| Example 60 | — | — | 49.8 | — |
| Example 61 | — | — | >100 | — |
| Example 62 | — | — | >100 | — |
| Example 63 | — | — | >100 | — |
| Example 64 | — | — | 29.2 | — |
| Example 65 | — | — | >100 | — |
| Example 66 | — | — | >100 | — |
| Example 67 | — | — | 50.7 | — |
| Example 68 | — | — | 53.1 | — |
| Example 69 | — | — | 68.5 | — |
| Example 70 | — | — | 13.5 | — |
| Example 71 | — | — | 6.9 | — |
| Example 72 | — | — | 8.8 | — |
| Example 74 | — | — | 6.850 | — |
| Example 75 | — | — | 8.207 | — |
| Example 76 | — | — | 3.121 | — |
| Example 77 | — | — | >100 | — |
| Example 78 | — | — | >100 | — |
| Example 79 | — | — | >100 | — |
| Example 80 | — | — | >100 | — |
| Example 81 | — | — | >100 | — |
| Example 82 | — | — | >100 | — |
| Example 83 | — | — | 56.8 | — |
| Example 84 | — | — | 27.4 | — |
| Example 85 | — | — | 28.8 | — |
| Example 86 | — | — | 53.2 | — |
| Example 87 | — | — | 2.573 | — |
| Example 88 | — | — | 7.415 | — |
| Example 89 | — | — | 59.46 | 44% |
| Example 90 | — | — | 27.73 | — |
| Example 91 | — | — | 11.04 | — |
| Example 92 | — | — | >100 | — |
| Example 93 | — | — | >100 | — |
| Example 94 | — | — | >100 | — |
| Example 95 | — | — | >100 | — |
| Example 96 | — | — | >100 | — |

What is claimed is:

1. A compound of Chemical Formula 1, or a pharmaceutically acceptable salt thereof:

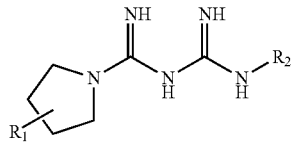

[Chemical Formula 1]

wherein, $R_1$ is hydrogen, a hydroxy group, or a linear or branched $C_{1-6}$ alkyl which can be substituted by hydrogen or a hydroxy group, $R_2$ has Chemical Formula 11

[Chemical Formula 11]

wherein $R_3$ is a linear or branched $C_1$-$C_6$ alkyl, $R_4$ is an amine; $C_1$-$C_6$ alkylamine; or amide, and, m is 1, 2 or 3.

2. A compound selected from the group consisting of:
N1-pyrrolidine-N5-(benzo[1,3]dioxol-5-ylmethyl) biguanide,
N1-pyrrolidine-N5-(4-methoxy)phenyl biguanide,
N1-pyrrolidine-N5-(3-chloro-4-methoxy)phenyl biguanide,
N1-pyrrolidine-N5-(2,6-difluoro-N5-methyl)phenyl biguanide,
N1-pyrrolidine-N5-(4-dimethylamino)phenyl biguanide,
N1-pyrrolidine-N5-(4-isopropyl)phenyl biguanide,
N1-pyrrolidine-N5-(3-phenoxy)phenyl biguanide,
N1-pyrrolidine-N5-(N-biphenyl-3-yl) biguanide,
N1-pyrrolidine-N5-(N-biphenyl-4-yl) biguanide,
N1-pyrrolidine-N5-(4-fluorobiphenyl-3-yl) biguanide,
N1-pyrrolidine-N5-(3-fluorobiphenyl-4-yl) biguanide,
N1-pyrrolidine-N5-(4-fluoro)phenethyl biguanide,
N1-pyrrolidine-N5-(2-phenylpropane-2-yl) biguanide,
N1-pyrrolidine-N5-(5,6,7,8-tetrahydronaphthalene-2-yl) biguanide,
N1-pyrrolidine-N5-((1,2,3,4-tetrahydronaphthalene-1-yl) biguanide,
N1-(S)-2-methyl pyrrolidine-N5-(4-(trifluoromethoxy) phenyl biguanide,
N1-(S)-3-hydroxy pyrrolidine-N5-(4-(trifluoromethoxy) phenyl biguanide,
N1-(R)-3-hydroxy pyrrolidine-N5-(4-(trifluoromethoxy) phenyl biguanide,
N-ethyl-4-((3-(imino(pyrrolidin-1-yl)methyl)guanidino) methyl)benzamide,
N-ethyl-3-((3-(imino(pyrrolidin-1-yl)methyl)guanidino) methyl)benzamide,
N1-pyrrolidine-N5-(4-(2-aminoethyl)phenyl biguanide,
N—(N-(4-(2-oxo-2-(piperidin-1-yl)ethylthio)phenyl)carbamimidoyl)pyrrolidine-1-carboximidamide, and
(S)-3-hydroxy-N—(N-(4-(2-oxo-2-(piperidin-1-yl)ethylthio)phenyl)carbamimidoyl)pyrrolidine-1-carboximidaide.

3. The compound according to claim 1, wherein the pharmaceutically acceptable salt is an acid addition salt of an acid selected from the group consisting of formic acid, acetic acid, propionic acid, lactic acid, butyric acid, isobutyric acid, triflouroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid and boric acid.

4. A pharmaceutical composition comprising the compound according to claim 1 or a pharmaceutical salt thereof as an active ingredient, and a pharmaceutically acceptable carrier.

* * * * *

UNITED STATES PATENT AND TRADEMARK OFFICE
CERTIFICATE OF CORRECTION

PATENT NO. : 10,221,190 B2
APPLICATION NO. : 14/528468
DATED : March 5, 2019
INVENTOR(S) : Hong Woo Kim Page 1 of 1

It is certified that error appears in the above-identified patent and that said Letters Patent is hereby corrected as shown below:

In the Specification

Column 3, Line 14, replace "does not contravenes" with --does not contravene--.

Column 5, Line 27, replace "$(R_{21})_s$" with --$(R_{21})_t$--.

Column 17, Line 55, replace "a an" with --an--.

Column 20, Line 42, replace "amine" with --amine.--;
    Line 64, replace "amine" with --amine.--.

Column 24, Line 18, replace "$^1$H (600" with --$^1$H NMR (600--.

Column 54, Line 63, replace "amine" with --amine.--.

Column 55, Line 20, replace "amine" with --amine.--.

Column 56, Line 18, replace "diamine" with --diamine.--.

In the Claims

Column 60, Line 41, Claim 2 replace "N5-(4-fluoro" with --N5-(4'-fluoro--;
    Line 42, Claim 2 replace "N5-(3-fluoro" with --N5-(3'-fluoro--.

Signed and Sealed this
Twenty-fourth Day of March, 2020

Andrei Iancu
*Director of the United States Patent and Trademark Office*